(12) United States Patent
Jagtap

(10) Patent No.: US 8,501,708 B2
(45) Date of Patent: Aug. 6, 2013

(54) ADENOSINE COMPOUNDS AND THEIR USE THEREOF

(75) Inventor: Prakash Jagtap, N. Andover, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 21 days.

(21) Appl. No.: 13/071,993

(22) Filed: Mar. 25, 2011

(65) Prior Publication Data

US 2011/0245194 A1    Oct. 6, 2011

(51) Int. Cl.
*A61K 31/70* (2006.01)
*C07H 19/167* (2006.01)
*C07H 19/173* (2006.01)

(52) U.S. Cl.
USPC .......................................... 514/46; 536/27.62

(58) Field of Classification Search
None
See application file for complete search history.

(56) References Cited

U.S. PATENT DOCUMENTS

| | | | |
|---|---|---|---|
| 7,271,157 B2 * | 9/2007 | Elzein et al. | 514/46 |
| 7,423,144 B2 | 9/2008 | Jagtap et al. | |
| 7,713,946 B2 * | 5/2010 | Dhalla et al. | 514/46 |
| 2006/0009417 A1 | 1/2006 | Elzein et al. | |
| 2007/0185051 A1 | 8/2007 | Dhalla et al. | |

FOREIGN PATENT DOCUMENTS

| | | |
|---|---|---|
| WO | 93/23418 A1 | 11/1993 |
| WO | 2009/100326 A1 | 8/2009 |

OTHER PUBLICATIONS

Avila, Marcel Y. et al., "A1-, A2A- and A3-subtype adenosine receptors modulate intraocular pressure in the mouse," British Journal of Pharmacology, vol. 134:241-245 (2001).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E. et al., "Characterization of Ocular Hypertension Induced by Adenosine Agonists," Investigative Ophthalmology & Visual Science, vol. 37(9):1833-1839 (1996).
Dalpiaz, Alessandro et al., "Fabrication Via a Nonaqueous Nanoprecipitation Method, Characterization and In Vitro Biological Behavior of N6-Cyclopentyladenosine-Loaded Nanoparticles," Journal of Pharmaceutical Sciences, vol. 98 (11):4272-4284 (2009).
Elzein, Elfatih et al., "A1 adenosine receptor agonists and their potential therapeutic applications," Expert Opinion on Investigational Drugs, vol. 17(12):1901-1910 (2008).
Fredholm, Bertil B. et al., "International Union of Pharmacology. XXV. Nomenclature and Classification of Adenosine Receptors," Pharmacological Reviews, vol. 53(4):527-552 (2001).
Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1):258-265 (2007).
Konno, Takashi et al., "2-(1-Hexyn-1-yl)adenosine-induced intraocular hypertension is mediated via K+ channel opening through adenosine A2A receptor in rabbits," European Journal of Pharmacology, vol. 518:203-211 (2005).
Konno, Takashi et al., "Effect of chymase on intraocular pressure in rabbits," European Journal of Pharmacology, vol. 524:132-137 (2005).
Konno, Takashi et al., "Involvement of Adenosine A2a Receptor in Intraocular Pressure Decrease Induced by 2-(1-Octyn-1-yl)adenosine or 2-(6-Cyano-1-hexyn-1-yl)adenosine," J. Pharmacol. Sci., vol. 97:501-509 (2005).
Ralevic, Vera et al., "Receptors for Purines and Pyrimidines," Pharmacological Reviews, vol. 50(3):413-492 (1998).
Tian, Baohe et al., "Effects of Adenosine Agonists on Intraocular Pressure and Aqueous Humor Dynamics in Cynomolgus Monkeys," Exp. Eye Res., vol. 64:979-989 (1997).
Tsilimbaris, Miltiadis K. et al., "The Use of Atomic Force Microscopy for the Observation of Corneal Epithelium Surface," Invest Ophthalmol. Vis. Sci., vol. 41:680-686 (2000).
International Search Report and Written Opinion for Application No. PCT/US2011/029929, dated Jun. 9, 2011.

* cited by examiner

*Primary Examiner* — Lawrence E Crane
(74) *Attorney, Agent, or Firm* — Nelson Mullins Roley & Scarborough LLP; Jane E. Remillard, Esq.; Cynthia L. Kanik

(57) ABSTRACT

Provided herein are a class of purine nucleoside compounds, particularly substituted adenosine compounds, such as benzyloxy cyclopentyladenosine (BCPA) compounds, as well as methods of using these compounds as selective $A_1$ adenosine receptor agonists, particularly for reducing and/or controlling elevated or abnormally fluctuating intraocular pressure (IOP) in the treatment of glaucoma or ocular hypertension (OHT).

39 Claims, 2 Drawing Sheets

ADENOSINE COMPOUNDS AND THEIR USE THEREOF

CROSS-REFERENCE TO RELATED APPLICATIONS

This application claims priority to U.S. Provisional Application No. 61/317,972, filed Mar. 26, 2010. The entire contents of the aforementioned application and any patents, patent applications, and references cited throughout this specification are herein incorporated by reference in their entireties.

TECHNICAL FIELD OF THE INVENTION

Provided herein are benzyloxy cycloalkyladenosine (BCAA) compounds and their use as selective A1 adenosine receptor agonists. In one embodiment, these compounds are directed to use in subjects for reducing and/or controlling elevated or abnormally fluctuating intraocular pressure (TOP) in the treatment of glaucoma or ocular hypertension (OHT). Specifically, the benzyloxy cycloalkyladenosine compounds include $N^6$-(2-benzyloxycyclopentyl)adenosine (BCPA) and $N^6$-(2-benzyloxycyclohexyl)adenosine (BCHA) compounds according to Formula I.

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated IOP is a major risk factor for glaucoma and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

OHT is a condition in which IOP is elevated but no glaucomatous findings have been observed (Bell, 2005). The Ocular Hypertension Study demonstrated that patients with OHT have an overall risk of 10% over 5 years of developing glaucoma and that this risk can be cut in half by the institution of medical treatment that reduces IOP. Drug therapies that have proven to be effective for the reduction of intraocular pressure include both agents that decrease aqueous humor production and agents that increase the outflow facility. Such therapies are in general administered by one of two possible routes: topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes, irises, and periorbital tissues. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies.

SUMMARY OF THE INVENTION

There remains a need for new treatments and therapies for elevated intraocular pressure (TOP), and conditions caused by elevated IOP. There is also a need for compounds useful in the treatment or prevention or amelioration of one or more symptoms of elevated IOP and conditions caused by elevated IOP.

In a first aspect, the present invention provides a compound of Formula I

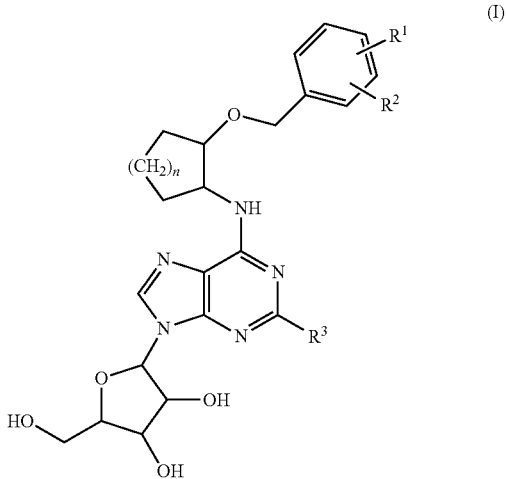

or a pharmaceutically acceptable salt thereof,
wherein, $R^1$ and $R^2$ are independently selected from —H, —$C_1$-$C_6$alkyl, -halo, or —O($C_1$-$C_6$)alkyl; $R^3$ is selected from —H, -halo or —CN; and n is 1 or 2, with the proviso that the compound of Formula I is not the following compound:

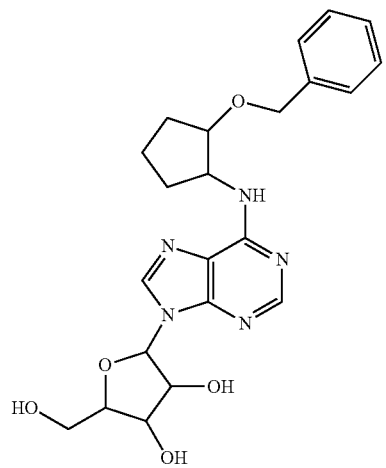

In a further aspect of the invention there is provided a method of treating or preventing a condition wherein said condition is mitigated through activation of the adenosine A1 receptor using an effective amount of a compound of Formula I

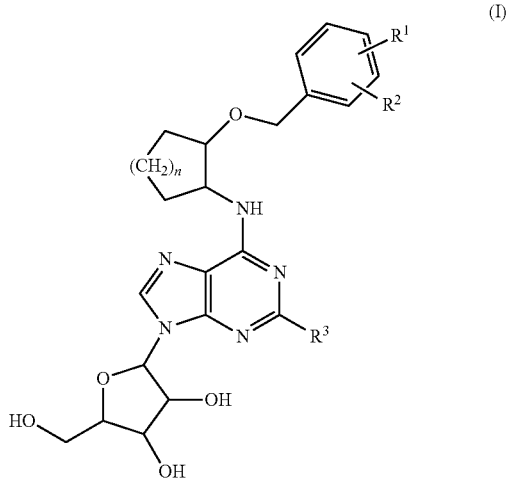

or a pharmaceutically acceptable salt thereof.

In one embodiment, the method includes slowing a subject's metabolic rate, protecting a subject's heart against myocardial damage during cardioplegia, treating a cardiovascular disease including cardiac arrhythmia, congestive heart failure, or cardiomyopathy, reducing pain, (ii) treating or preventing elevated IOP; or (ii) reducing IOP in a subject.

In a further aspect there is provided the use of a compound of Formula I or a pharmaceutically acceptable salt thereof as an antinociceptive, antilipolytic or an anitanginal agent.

In a further aspect of the invention there is provided a method of reducing intraocular pressure comprising the step of: delivering an effective amount of a compound of Formula I or a pharmaceutically acceptable salt thereof to the anterior chamber of an affected eye of a subject.

In one embodiment the method of reducing intraocular pressure comprising the step of: delivering an effective amount of a compound of Formula I or a pharmaceutically acceptable salt thereof to the anterior chamber of an affected eye of a subject, wherein the compound of Formula (I) or a pharmaceutically acceptable salt thereof is selected from the following:

2-(6-(2-(benzyloxy)cyclopentylamino)-9H-purin-9-yl)-5-(hydroxymethyl)tetrahydrofuran-3,4-diol;

2-(6-(2-(benzyloxy)cyclohexylamino)-9H-purin-9-yl)-5-(hydroxymethyl)tetrahydrofuran-3,4-diol;

2-(hydroxymethyl)-5-(6-(2-(4-methylbenzyloxy)cyclopentylamino)-9H-purin-9-yl)tetrahydrofuran-3,4-diol;

2-(hydroxymethyl)-5-(6-(2-(3-methylbenzyloxy)cyclopentylamino)-9H-purin-9-yl)tetrahydrofuran-3,4-diol;

2-(hydroxymethyl)-5-(6-(2-(2-methylbenzyloxy)cyclopentylamino)-9H-purin-9-yl)tetrahydrofuran-3,4-diol;

2-(6-(2-(3-fluorobenzyloxy)cyclopentylamino)-9H-purin-9-yl)-5-(hydroxymethyl)tetrahydrofuran-3,4-diol;

2-(6-(2-(4-fluorobenzyloxy)cyclopentylamino)-9H-purin-9-yl)-5-(hydroxymethyl)tetrahydrofuran-3,4-diol;

2-(hydroxymethyl)-5-(6-(2-(4-isopropylbenzyloxy)cyclopentylamino)-9H-purin-9-yl)tetrahydrofuran-3,4-diol;

2-(hydroxymethyl)-5-(6-(2-(3-iodobenzyloxy)cyclopentylamino)-9H-purin-9-yl)tetrahydrofuran-3,4-diol;

2-(hydroxymethyl)-5-(6-(2-(3-methoxybenzyloxy)cyclopentylamino)-9H-purin-9-yl)tetrahydrofuran-3,4-diol;

2-(2-chloro-6-(2-(3-methylbenzyloxy)cyclopentylamino)-9H-purin-9-yl)-5-(hydroxymethyl)tetrahydrofuran-3,4-diol;

2-(2-chloro-6-(2-(2-methylbenzyloxy)cyclopentylamino)-9H-purin-9-yl)-5-(hydroxymethyl)tetrahydrofuran-3,4-diol;

2-(2-chloro-6-(2-(4-fluorobenzyloxy)cyclopentylamino)-9H-purin-9-yl)-5-(hydroxymethyl)tetrahydrofuran-3,4-diol;

2-(2-chloro-6-(2-(4-isopropylbenzyloxy)cyclopentylamino)-9H-purin-9-yl)-5-(hydroxymethyl)tetrahydrofuran-3,4-diol;

2-(hydroxymethyl)-5-(6-(2-(2,6-dimethylbenzyloxy)cyclopentylamino)-9H-purin-9-yl)tetrahydrofuran-3,4-diol, and 2-(hydroxymethyl)-5-(6-(2-(2,5-dimethylbenzyloxy)cyclopentylamino)-9H-purin-9-yl)tetrahydrofuran-3,4-diol.

In one embodiment the method comprises the step of applying about 0.05 mg/ml to about 7.0 mg/ml of a compound according to Formula I from 1 to 4 times daily, or in another embodiment the method comprises the step of applying about 20-700 µg of a compound according to Formula I from 1 to 2 times daily or in another embodiment the method comprises the step of applying about 350 µg of a compound according to Formula I from 1 to 2 times daily.

In one embodiment the IOP of the affected eye is reduced by at least 10%. In another embodiment the IOP of the affected eye is reduced by at least 10-20%.

In a further embodiment the IOP of the affected eye is reduced by 20% or more.

In one embodiment the IOP of the affected eye is reduced by at least 10% for more than 3 hours, in another embodiment the IOP of the affected eye is reduced by at least 10-20% for more than 3 hours, in a further embodiment the IOP of the affected eye is reduced by 20% or more for more than 3 hours and in another embodiment the IOP of the affected eye is reduced by at least 10% for at least 6 hours.

In another aspect the method as defined above further comprises the prior, simultaneous or sequential, application of a second IOP reducing agent. In one embodiment the second IOP reducing agent is selected from the group comprising: β-blockers, prostaglandin analog, prostamides, carbonic anhydrase inhibitors, rho-kinase inhibitors, $\alpha_2$ agonists, miotics, neuroprotectants, $A_1$ agonist, $A_3$ antagonists, $A_2A$ agonists and combinations thereof.

In one embodiment the effective amount of the compound of Formula I is administered as a single dose.

In one embodiment the effective amount of the compound of Formula I is administered as a twice daily dose.

In another aspect there is provided an ophthalmic pharmaceutical composition comprising a compound of Formula I as defined above and a pharmaceutically acceptable vehicle or excipient.

In one embodiment the pharmaceutically acceptable vehicle or excipient is selected from the group comprising of: ophthalmologically acceptable preservatives, surfactants, viscosity enhancers, penetration enhancers, gelling agents, hydrophobic bases, vehicles, buffers, sodium chloride, and water.

In one embodiment the composition further comprises a second IOP reducing agent in addition to a compound of Formula I as defined above. The second IOP reducing agent is selected from the group comprising: β-blockers, prostaglandin analogs, prostamides, carbonic anhydrase inhibitors, rho-kinase inhibitors, $\alpha_2$ agonists, miotics, neuroprotectants, $A_1$ agonists, $A_3$ antagonists, $A_2A$ agonists and combinations thereof.

It is to be further appreciated that the use of a compound of Formula I as defined above, or ophthalmic compositions as defined above may be used for manufacture of a medicament for reducing IOP in an affected eye of a subject.

It is recognized that compounds of Formula I can contain one or more chiral centers.

This invention contemplates all enantiomers, diastereomers, and mixtures of Formulas I thereof.

Furthermore, certain embodiments of the present invention comprise pharmaceutically acceptable salts of compounds according to Formula I.

Pharmaceutically acceptable salts comprise, but are not limited to, soluble or dispersible forms of compounds according to Formula I that are suitable for treatment of disease without undue undesirable effects such as allergic reactions or toxicity.

Representative pharmaceutically acceptable salts include, but are not limited to, acid addition salts such as acetate, citrate, benzoate, lactate, or phosphate and basic addition salts such as lithium, sodium, potassium, or aluminum.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1A:
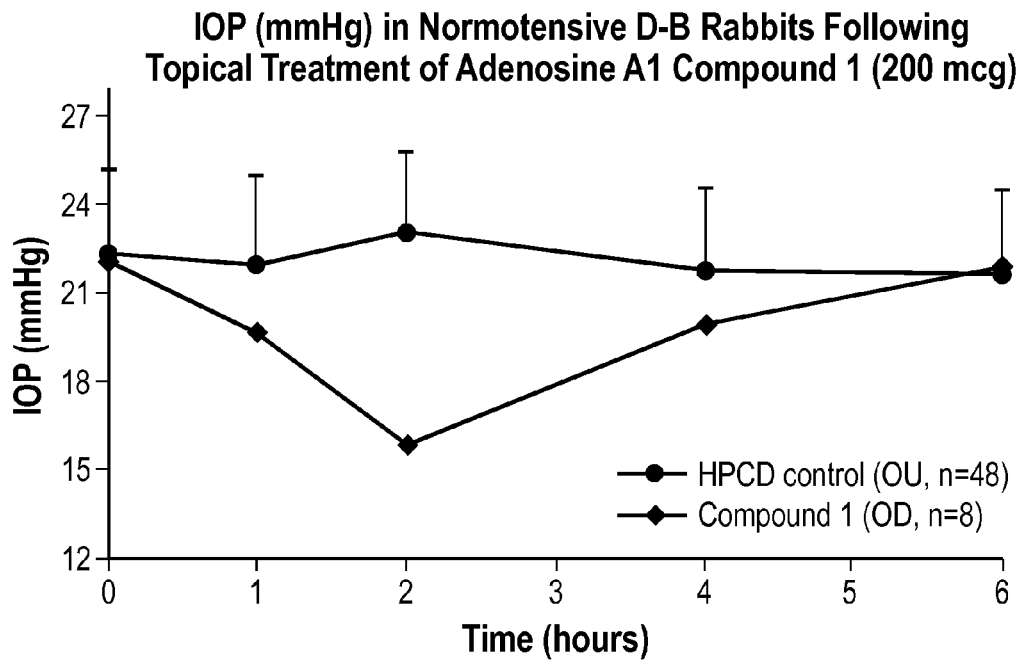
FIG. 1a: shows the IOP (mmHg) changes over time in the study eye of a group of Normotensive Dutch-Belted rabbits after administration of a topical single dose of 200 mcg of Compound 1 relative to hydroxylpropyl β-cyclodextrin (HPCD) control group.
Figure 1B:
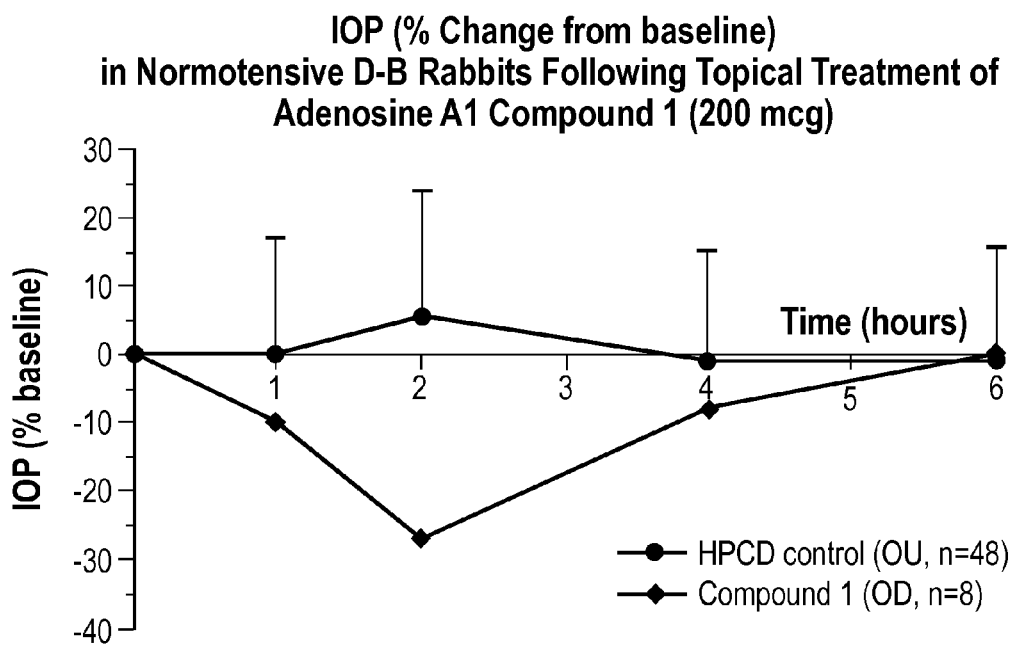
FIG. 1b: shows the IOP (% change from baseline) changes over time in the study eye of a group of Normotensive Dutch-Belted rabbits after administration of a topical single dose of 200 mcg of Compound 1 relative to HPCD control group.

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

DEFINITIONS

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —CF$_3$, —NO$_2$, —ONO$_2$, —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_{10}$ optionally branched aliphatic" as used herein refers to a straight or branched chain; optionally unsaturated hydrocarbon having from 1 to 10 carbon atoms.

Representative $C_1$-$C_{10}$ aliphatic groups include, but are not limited to ethylene, isopropylene, propyne, butyne, sec-butylene, pentylene, hexyldiene, heptylene, heptyne, octylene, octyne.

The term "$C_1$-$C_6$ alkyl" as used herein refers to a straight or branched chain; saturated hydrocarbon having from 1 to 6 carbon atoms. Representative $C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, and neohexyl. Unless indicated, the $C_1$-$C_6$ alkyl is unsubstituted.

The term "aryl" as used herein refers to a phenyl group or a naphthyl group. In one embodiment, the aryl group is substituted with one or more of the following groups: —OH or OH—$C_1$-$C_6$alkyl groups. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl, cyclooctyl and norbornyl. In one embodiment, the $C_3$-$C_8$ monocyclic cycloalkyl group is substituted with one or more of the following groups: OH or OH—$C_1$-$C_6$alkyl groups. Unless indicated, the $C_3$-$C_8$ monocyclic cycloalkyl is unsubstituted.

The term "effective amount" as used herein refers to an amount of Formula I that is effective for: (i) treating or preventing a condition whereby agonism of the A1 receptor is desirable, including slowing a subject's metabolic rate, protecting a subject's heart against myocardial damage during cardioplegia, treating a cardiovascular disease including cardiac arrhythmia, congestive heart failure, or cardiomyopathy, reducing pain, (ii) treating or preventing elevated IOP; or (ii) reducing IOP in a subject.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom.

The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl. In one embodiment, the 3- to 7-membered monocyclic heterocycle group is substituted with one or more of the following groups: OH or OH—$C_1$-$C_6$alkyl groups. Unless indicated, the 3- to 7-membered monocyclic heterocycle is unsubstituted.

The phrase "pharmaceutically acceptable salt," as used herein, is a salt of an acid and a basic nitrogen atom of a purine compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound.

Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "subject" as used herein includes all mammals, such as human, mouse, rat, rabbit, dog, horse, cow, pig and monkey.

The following abbreviations are used herein and have the indicated definitions: HPCD or HPβCD is Hydroxypropyl β-Cyclodextrin, USP; NMR is nuclear magnetic resonance; OHT is ocular hypertension or POAG is primary open-angle glaucoma.

The term "treat" is used herein to mean to relieve, reduce or alleviate at least one symptom of a disease in a subject. For example, in relation to glaucoma, the term "treat" may mean to reduce or alleviate elevated intraocular pressure. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "subject" is intended to include animals, which are capable of suffering from or afflicted with elevated IOP, as well as conditions caused by elevated IOP.

Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from IOP, or conditions caused by elevated IOP.

The term "about" or "approximately" usually means within 20%, more preferably within 10%, and most preferably still within 5% of a given value or range.

Alternatively, especially in biological systems, the term "about" means within about a log (i.e., an order of magnitude) preferably within a factor of two of a given value. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. Embodiments of the present invention define compounds of Formula I that are selective adenosine A1 receptor agonists.

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J. Pharmacol. 134:241-245, 2001). While other publications have noted that adenosine A1 receptor agonists in the eye target the conventional outflow pathway via the trabecular meshwork (Husain S et al. J Pharmacol Exp Ther. 320: 258-265, 2007), reduction of IOP via other pathways has not been excluded.

It should be noted that the highly robust, adenosine $A_1$ receptor-mediated drop in IOP reported in preclinical studies is often preceded by an immediate, yet transient elevation in IOP following instillation of the $A_1$ receptor ligand (Crosson C E and Grey T. Inv Ophthal Visual Sci. 37, [9] 1833-1839, 1996). Transient elevations in IOP of ~3-9 mmHg have been observed in a ~30 min "window" after dosing. This phenomenon may arise from cross-reactivity between adenosine receptor sub-types within the eye. Pharmacological studies indicate that this transient elevation in IOP might be due, at least in part, to the activation of adenosine $A_{2B}$ receptors (Crosson, 1996). Therefore, development of a highly-selective A$_1$ agonist that only reduce IOP would appear to be more tenable than the development of adenosine A$_2$-receptor-based drugs for treating IOP, as A$_{2A}$ agonists may increase, decrease or exert mixed effects on IOP (Konno, 2004; Konno, J Pharmacol Sci., 2005; Konno, Eur J. Pharmacol. 2005).

A$_1$ agonists are known to play a role in conditions such as acute and chronic disorders of heart rhythym, non-insulin-dependent diabetes mellitus, decreased insulin sensitivity, and to have a use as an antinociceptive, antilipolytic or an anitanginal agent. Elzein, 2008, Expert Opin. Invest. Drugs, 1901-1910.

Compounds that act as selective adenosine A$_1$ agonists are known and have shown a variety of utilities. U.S. Pat. No. 7,423,144 to Jagtap et al. describes such selective adenosine A1 agonist compounds for the prevention or treatment of tachyarrhythmias (elevated heart rate), pain disorders, and ischemia-reperfusion injury.

The following compound:

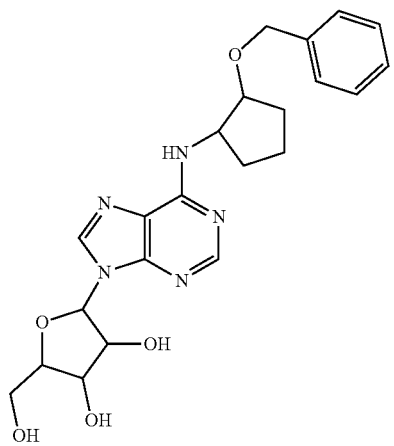 [SMILES: OCC1OC(n2cnc3c(NC4CCCC4OCc4ccccc4)ncnc32)C(O)C1O]

has been described in US2006/009417A1 and US2007/0185051A1 as an intermediate compound in a synthetic scheme to prepare A$_1$ Adenosine receptor compounds of the general structure:

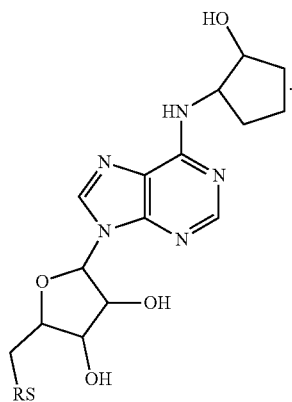

It has now been found that an additional class of compounds of Formula I are selective adenosine A$_1$ receptor agonists.

Compounds of Formula I are of the structure:

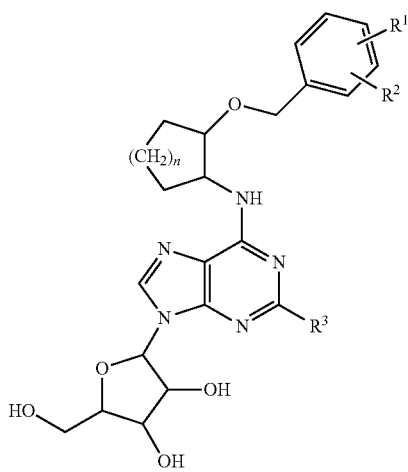

wherein R$^1$ and R$^2$ are independently selected from —H, —C$_1$-C$_6$alkyl, -halo, or —O(C$_1$-C$_6$)alkyl; R$^3$ is selected from —H, -halo or —CN; and n is 1 or 2. In one embodiment, the compound of Formula I is not the following compound:

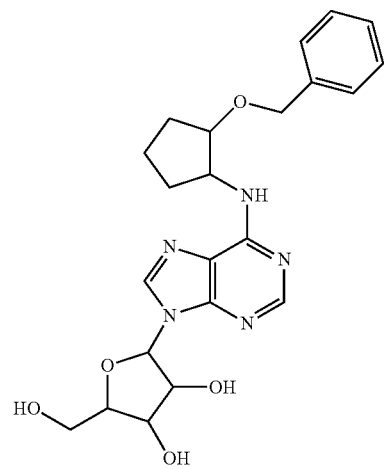 [SMILES: OCC1OC(n2cnc3c(NC4CCCC4OCc4ccccc4)ncnc32)C(O)C1O]

or any stereoisomer thereof.

In one embodiment n is 1, R$^1$ is —C$_1$-C$_6$alkyl, R$^2$ is —H and R$^3$ is —H.

In one embodiment n is 1, R$^1$ is —H, R$^2$ is —H and R$^3$ is -halo.

In one embodiment n is 1, R$^1$ is —H, R$^2$ is —H and R$^3$ is —Cl.

In one embodiment n is 1, R$^1$ is —CH(CH$_3$)$_2$, R$^2$ is —H and R$^3$ is —H.

In one embodiment n is 1, R$^1$ is —CH$_3$, R$^2$ is —H and R$^3$ is —H.

In another embodiment n is 1, R$^1$ is —CH$_3$, R$^2$ is —H and R$^3$ is -halo.

In one embodiment n is 1, R$^1$ is —CH$_3$, R$^2$ is —H and R$^3$ is —Cl.

In another embodiment n is 1, R$^1$ is halo, R$^2$ is —H and R$^3$ is -halo.

In another embodiment n is 1, R$^1$ is —F, R$^2$ is —H and R$^3$ is —Cl.

In one embodiment n is 1, R$^1$ is —CH(CH$_3$)$_2$, R$^2$ is —H and R$^3$ is -halo.

In another embodiment n is 1, R¹ is halo, R² is —H and R³ is H.

In one embodiment n is 1, R¹ is —F, R² is —H and R³ is H.

In another embodiment n is 1, R¹ is —I, R² is —H and R³ is H.

In another embodiment n is 1, R¹ is —O(C₁-C₆)alkyl, R² is —H and R³ is H.

In another embodiment n is 1, R¹ is —OCH₃, R² is —H and R³ is H.

In another embodiment n is 1, R¹ is —CH₃, R² is —CH₃ and R³ is H.

In one embodiment n is 2, R¹ is —H, R² is —H and R³ is H.

In one embodiment n is 2, R¹ is —H, R² is —H and R³ is -halo.

In one embodiment n is 2, R¹ is —H, R² is —H and R³ is —Cl.

In one embodiment n is 2, R¹ is —CH(CH₃)₂, R² is —H and R³ is H.

In one embodiment n is 2, R¹ is —CH₃, R² is —H and R³ is H.

In another embodiment n is 2, R¹ is —CH₃, R² is —H and R³ is -halo.

In one embodiment n is 2, R¹ is —CH₃, R² is —H and R³ is —Cl.

In another embodiment n is 2, R¹ is halo, R² is —H and R³ is -halo.

In another embodiment n is 2, R¹ is —F, R² is —H and R³ is —Cl.

In one embodiment n is 2, R¹ is —CH(CH₃)₂, R² is —H and R³ is -halo.

In another embodiment n is 2, R¹ is halo, R² is —H and R³ is H.

In one embodiment n is 2, R¹ is —F, R² is —H and R³ is H.

In another embodiment n is 2, R¹ is —I, R² is —H and R³ is H.

In another embodiment n is 2, R¹ is —O(C₁-C₆)alkyl, R² is —H and R³ is H.

In another embodiment n is 2, R¹ is —OCH₃, R² is —H and R³ is H.

In another embodiment n is 2, R¹ is —CH₃, R² is —CH₃ and R³ is H.

In one embodiment the compound of Formula I is selected from the following:

2-(6-(2-(benzyloxy)cyclohexylamino)-9H-purin-9-yl)-5-(hydroxymethyl)tetrahydrofuran-3,4-diol;

2-(hydroxymethyl)-5-(6-(2-(4-methylbenzyloxy)cyclopentylamino)-9H-purin-9-yl)tetrahydrofuran-3,4-diol;

2-(hydroxymethyl)-5-(6-(2-(3-methylbenzyloxy)cyclopentylamino)-9H-purin-9-yl)tetrahydrofuran-3,4-diol;

2-(hydroxymethyl)-5-(6-(2-(2-methylbenzyloxy)cyclopentylamino)-9H-purin-9-yl)tetrahydrofuran-3,4-diol;

2-(6-(2-(3-fluorobenzyloxy)cyclopentylamino)-9H-purin-9-yl)-5-(hydroxymethyl)tetrahydrofuran-3,4-diol;

2-(6-(2-(4-fluorobenzyloxy)cyclopentylamino)-9H-purin-9-yl)-5-(hydroxymethyl)tetrahydrofuran-3,4-diol;

2-(hydroxymethyl)-5-(6-(2-(4-isopropylbenzyloxy)cyclopentylamino)-9H-purin-9-yl)tetrahydrofuran-3,4-diol;

2-(hydroxymethyl)-5-(6-(2-(3-iodobenzyloxy)cyclopentylamino)-9H-purin-9-yl)tetrahydrofuran-3,4-diol;

2-(hydroxymethyl)-5-(6-(2-(3-methoxybenzyloxy)cyclopentylamino)-9H-purin-9-yl)tetrahydrofuran-3,4-diol;

2-(2-chloro-6-(2-(3-methylbenzyloxy)cyclopentylamino)-9H-purin-9-yl)-5-(hydroxymethyl)tetrahydrofuran-3,4-diol;

2-(2-chloro-6-(2-(2-methylbenzyloxy)cyclopentylamino)-9H-purin-9-yl)-5-(hydroxymethyl)tetrahydrofuran-3,4-diol;

2-(2-chloro-6-(2-(4-fluorobenzyloxy)cyclopentylamino)-9H-purin-9-yl)-5-(hydroxymethyl)tetrahydrofuran-3,4-diol;

2-(2-chloro-6-(2-(4-isopropylbenzyloxy)cyclopentylamino)-9H-purin-9-yl)-5-(hydroxymethyl)tetrahydrofuran-3,4-diol;

2-(hydroxymethyl)-5-(6-(2-(2,6-dimethylbenzyloxy)cyclopentylamino)-9H-purin-9-yl)tetrahydrofuran-3,4-diol, and 2-(hydroxymethyl)-5-(6-(2-(2,5-dimethylbenzyloxy)cyclopentylamino)-9H-purin-9-yl)tetrahydrofuran-3,4-diol.

In one embodiment, the compound of Formula I is Compound 11, or a pharmaceutically acceptable salt thereof.

In another embodiment, the compound of Formula I is Compound 17, or a pharmaceutically acceptable salt thereof.

In another embodiment, the compound of Formula I is Compound 18, or a pharmaceutically acceptable salt thereof.

In a further aspect of the invention there is provided a method of treating or preventing a condition wherein said condition is mitigated through activation of the adenosine A1 receptor using an effective amount of a compound of Formula I:

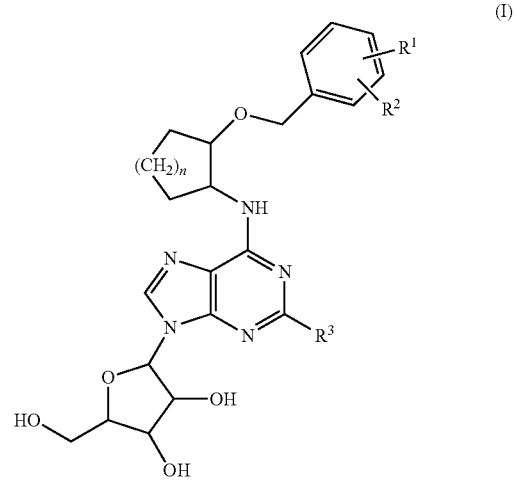

or a pharmaceutically acceptable salt thereof,
wherein, R¹ and R² are independently selected from —H, —C₁-C₆alkyl, -halo, or —O(C₁-C₆)alkyl; R³ is selected from —H, -halo or —CN; and n is 1 or 2.

In one embodiment of the method, n is 1, R¹ is —H, R² is —H and R³ is —H.

In one embodiment n is 1, R¹ is —H, R² is —H and R³ is -halo.

In one embodiment n is 1, R¹ is —H, R² is —H and R³ is —Cl.

In one embodiment n is 1, R¹ is —CH(CH₃)₂, R² is —H and R³ is —H.

In one embodiment n is 1, R¹ is —CH₃, R² is —H and R³ is —H.

In another embodiment n is 1, R¹ is —CH₃, R² is —H and R³ is -halo.

In one embodiment n is 1, R¹ is —CH₃, R² is —H and R³ is —Cl.

In another embodiment n is 1, R¹ is halo, R² is —H and R³ is -halo.

In another embodiment n is 1, R¹ is —F, R² is —H and R³ is —Cl.

In one embodiment n is 1, $R^1$ is —CH(CH$_3$)$_2$, $R^2$ is —H and $R^3$ is -halo.

In another embodiment n is 1, $R^1$ is halo, $R^2$ is —H and $R^3$ is H.

In one embodiment n is 1, $R^1$ is —F, $R^2$ is —H and $R^3$ is H.

In another embodiment n is 1, $R^1$ is —I, $R^2$ is —H and $R^3$ is H.

In another embodiment n is 1, $R^1$ is —O(C$_1$-C$_6$)alkyl, $R^2$ is —H and $R^3$ is H.

In another embodiment n is 1, $R^1$ is —OCH$_3$, $R^2$ is —H and $R^3$ is H.

In another embodiment n is 1, $R^1$ is —CH$_3$, $R^2$ is —CH$_3$ and $R^3$ is H.

In one embodiment of the method n is 2, $R^1$ is —H, $R^2$ is —H and $R^3$ is H.

In one embodiment n is 1, $R^1$ is —H, $R^2$ is —H and $R^3$ is -halo.

In one embodiment n is 1, $R^1$ is —H, $R^2$ is —H and $R^3$ is —Cl.

In one embodiment n is 2, $R^1$ is —CH(CH$_3$)$_2$, $R^2$ is —H and $R^3$ is H.

In one embodiment n is 2, $R^1$ is —CH$_3$, $R^2$ is —H and $R^3$ is H.

In another embodiment n is 2, $R^1$ is —CH$_3$, $R^2$ is —H and $R^3$ is -halo.

In one embodiment n is 2, $R^1$ is —CH$_3$, $R^2$ is —H and $R^3$ is —Cl.

In another embodiment n is 2, $R^1$ is halo, $R^2$ is —H and $R^3$ is -halo.

In another embodiment n is 2, $R^1$ is —F, $R^2$ is —H and $R^3$ is —Cl.

In one embodiment n is 2, $R^1$ is —CH(CH$_3$)$_2$, $R^2$ is —H and $R^3$ is -halo.

In another embodiment n is 2, $R^1$ is halo, $R^2$ is —H and $R^3$ is H.

In one embodiment n is 2, $R^1$ is —F, $R^2$ is —H and $R^3$ is H.

In another embodiment n is 2, $R^1$ is —I, $R^2$ is —H and $R^3$ is H.

In another embodiment n is 2, $R^1$ is —O(C$_1$-C$_6$)alkyl, $R^2$ is —H and $R^3$ is H.

In another embodiment n is 2, $R^1$ is —OCH$_3$, $R^2$ is —H and $R^3$ is H.

In another embodiment n is 2, $R^1$ is —CH$_3$, $R^2$ is —CH$_3$ and $R^3$ is H.

In one aspect of the method, the condition is elevated intraocular pressure.

In another aspect, the condition is ocular hypertension.

In yet another aspect, the condition is glaucoma.

In one aspect of the method, the condition is elevated intraocular pressure and the compound is Compound 1.

In another aspect, the condition is ocular hypertension and the compound is Compound 1.

In yet another aspect, the condition is glaucoma and the compound is Compound 1.

In one aspect of the method, the condition is elevated intraocular pressure and the compound is Compound 11.

In another aspect, the condition is ocular hypertension and the compound is Compound 11.

In yet another aspect, the condition is glaucoma and the compound is Compound 11.

In one aspect of the method, the condition is elevated intraocular pressure and the compound is Compound 17.

In another aspect, the condition is ocular hypertension and the compound is Compound 17.

In yet another aspect, the condition is glaucoma and the compound is Compound 17.

In one aspect of the method, the condition is elevated intraocular pressure and the compound is Compound 18.

In another aspect, the condition is ocular hypertension and the compound is Compound 18.

In yet another aspect, the condition is glaucoma and the compound is Compound 18.

In a further aspect of the invention there is provided a method of treating or preventing elevated intraocular pressure using an effective amount of a compound of Formula I.

In yet another aspect of the invention there is provided a method of treating or preventing ocular hypertension using an effective amount of a compound of Formula I.

In still another aspect of the invention there is provided a method of treating or preventing glaucoma using an effective amount of a compound of Formula I.

In one aspect of the method, the compound of Formula I is Compound 1.

In another aspect, the compound of Formula I is Compound 11.

In yet another aspect, the compound of Formula I is Compound 17.

In still another aspect, the compound of Formula I is Compound 18.

Formula I compounds may be delivered directly to the eye in a cornea permeable form (for example: topical ocular drops or ointments containing nanoparticles of compounds of Formula I; or via slow release devices such as pharmaceutical drug delivery sponges implanted in the cul-de-sac or implanted adjacent to the sclera or within the eye; periocular, conjunctival, sub-Tenon's, intracameral, intravitreal, or intracanalicular injections). It is further contemplated that the agents of the invention may be formulated in intraocular insert or implant devices. It is envisaged that a nonaqueous nanoprecipitation technique could be used to form nanparticles of a compound of Formula I having a particle size of less than 0.25 μm (less than 250 nm). The corneal epithelial junction gap has been measured by atomic force microscopy (AFM) as reported in The Use of Atomic Force Microscopy for the Observation of Corneal Epithelium Surface, Tsilimbaris et al., Investigative Ophthalmology & Visual Science, March 2000, Vol. 41, No. 3, pp. 680-686. A technique similar to that described by Dalpiaz et al. in Journal of Pharmaceutical Sciences, 2009, pages 1-13 would be suitable.

Formula I compounds may be delivered directly to the eye in a cornea permeable form (for example: topical ocular drops or ointments; or via slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections). It is further contemplated that the agents of the invention may be formulated in intraocular insert or implant devices.

The compounds of Formula I are preferably incorporated into topical ophthalmic formulations with a pH of about 4-8 for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity or solubility such as hydroxypropyl β-Cyclodextrin (HPβCD) or (HPCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in POAG or OHT patients. Such amounts are referred to herein as "an amount effective to control or reduce IOP," or more simply "an effective amount." The compounds will normally be contained in these formulations in an amount 0.05 mg/ml to 7.0 mg/ml but preferably in an amount of 0.4 to 7.0 mg/ml. Thus, for topical presentation 1 to 2 drops of these formulations would be delivered to the surface of the eye from 1 to 4 times per day, according to the discretion of a skilled clinician.

The compounds of Formula I can also be used in combination with other glaucoma treatment agents, such as, but not limited to, β-blockers, prostaglandin analogs, prostamides, carbonic anhydrase inhibitors, $\alpha_2$ agonists, miotics, and neuroprotectants, $A_1$ agonists, $A_3$ antagonists, $A_2A$ agonists and combinations thereof.

Synthesis

The BCPA esters were prepared according to the following procedure:

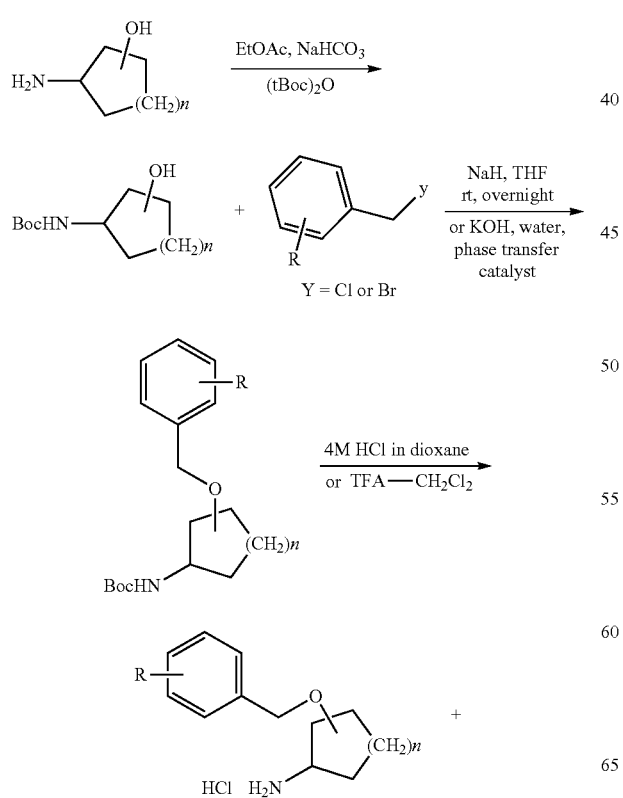

Procedure and Analytical Data:

A mixture of 6-chloropurine-9H-β-D-ribofuranoside (1 g, 3.5 mmol) and (1R,2R)-(−)-2-benzyloxycyclopentylamine (1.91 g, 3. eq.) in ethanol (15 ml) was refluxed for 16 h and the solution was concentrated. The resultant residue was dissolved in ethyl acetate (100 ml) and washed with water (15 ml×2) and dried over sodium sulfate. The mixture was then filtered and concentrated under vacuum. The crude residue obtained was purified twice on the silica gel column using methanol-dichloromethane (5:95) as an eluent. The pure fractions were combined and concentrated to provide white foam of the desired product (1.2 g).

Compound 1 (2R,3R,4S,5R)-2-(6-((1R,2R)-2-(benzyloxy)cyclopentylamino)-9H-purin-9-yl)-5-(hydroxymethyl)tetrahydrofuran-3,4-diol mp 150-152° C.; $^1$H NMR (CDCl$_3$) δ 1.52-2.02 (m, 5H), 2.29-2.32 (m, 1H), 3.03 (s, 1H), 3.68-3.76 (m, 1H), 3.90-3.95 (m, 2H), 4.32 (s, 1H), 4.43 (d, J=5.1 Hz, 1H), 4.64 (s, 2H), 4.98-5.04 (m, 1H), 5.75 (d, J=7.5 Hz, 1H), 5.83 (d, J=7.5 Hz, 1H), 6.60 (s, 1H), 7.23-7.31 (m, 6H), 7.74 (s, 1H), 8.24 (s, 1H); MS (CI) m/z 442.2 [M+1].

Following the above mentioned procedure following derivatives were prepared from the reaction of 6-chloropurine-9H-β-D-ribofuranoside or 2,6-dichloropurine-9H-β-D-ribofuranoside with corresponding 2-benzyloxy-cyclopentyl or cyclohexylamines.

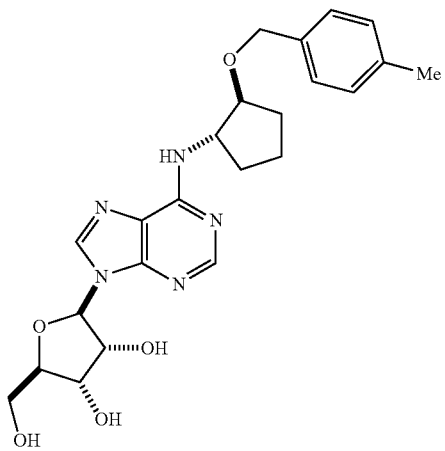

Compound 3: (2R,3S,4R,5R)-2-(hydroxymethyl)-5-(6-((1S,2S)-2-(4-methylbenzyloxy)cyclopentylamino)-9H-purin-9-yl)tetrahydrofuran-3,4-diol $^1$H NMR (DMSO-d$_6$-CDCl$_3$) δ 1.63-1.73 (m, 4H), 1.90-1.98 (m, 1H), 2.01-2.10 (m, 1H), 2.25 (s, 1H), 2.24-2.28 (m, 2H), 3.50-3.58 (m, 1H), 3.64-3.69 (m, 1H), 3.94-3.98 (m, 2H), 4.13-4.15 (m, 1H), 4.49 (s, 2H), 4.57-4.63 (dd, J=6.3 and 7.2 Hz, 2H), 5.20 (d, J=4.8 Hz, 1H), 5.41-5.46 (m, 2H), 5.88 (d, J=6.0 Hz, 1H), 7.08 (d, J=7.8 Hz, 2H), 7.14 (d, J=8.1 Hz, 2H), 7.94 (s, 1H), 8.23 (s, 1H), 8.36 (s, 1H); MS (CI) m/z 456.2 [M+1].

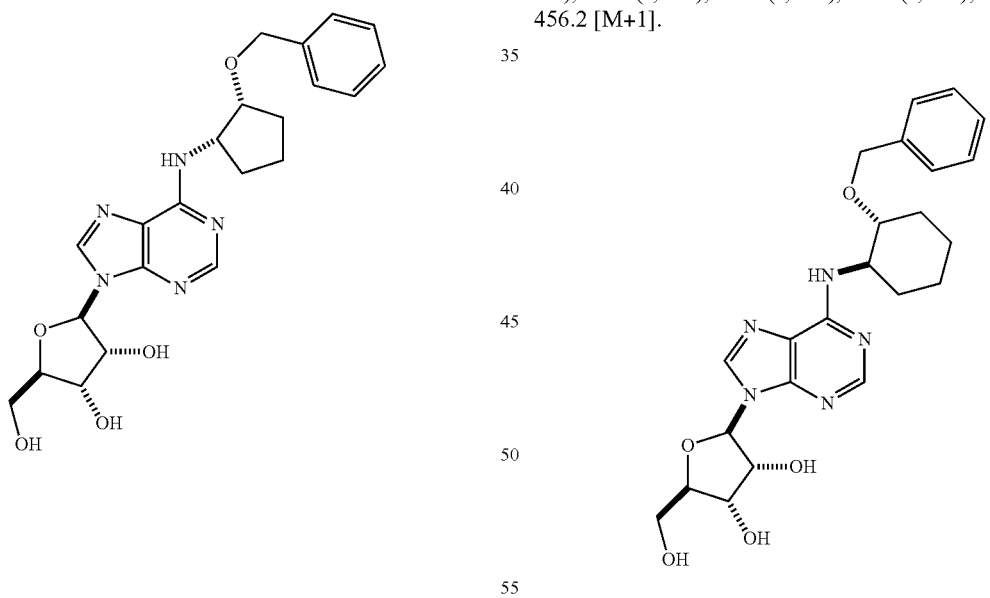

Compound 2: (2R,3R,4S,5R)-2-(6-((1S,2S)-2-(benzyloxy)cyclopentylamino)-9H-purin-9-yl)-5-(hydroxymethyptetrahydrofuran-3,4-diol $^1$H NMR (CDCl$_3$) δ 1.52-1.79 (m, 5H), 2.29-2.32 (m, 1H), 3.02 (s, 1H), 3.68-3.76 (m, 1H), 3.86-3.91 (m, 2H), 4.33 (s, 1H), 4.43 (d, J=4.2 Hz, 1H), 4.64 (d, J=3.3 Hz, 2H), 5.04-5.06 (m, 1H), 5.72-5.74 (m, 1H), 5.75 (d, J=7.2 Hz, 1H), 6.61 (m, 1H), 7.25-7.31 (m, 6H), 7.71 (s, 1H), 8.19 (s, 1H); MS (CI) m/z 442.2 [M+1].

Compound 4: (2R,3R,4S,5R)-2-(6-((1R,2R)-2-(benzyloxy)cyclohexylamino)-9H-purin-9-yl)-5-(hydroxymethyptetrahydrofuran-3,4-diol $^1$H NMR (CDCl$_3$) δ 1.25-1.84 (m, 8H), 2.15-2.21 (m, 2H), 2.95 (s, 1H), 3.32-3.38 (m, 1H), 3.71 (d, J=12.6 Hz, 1H), 3.93 (d, J=12.9 Hz, 1H), 4.31 (s, 1H), 4.41 (d, J=5.1 Hz, 1H), 4.47 (d, J=12 Hz, 1H), 4.64 (d, J=12 Hz, 1H), 4.98-5.04 (m, 1H), 5.75 (d, J=7.5 Hz, 1H), 5.80 (s, 1H), 7.18-7.28 (m, 5H), 7.75 (s, 1H), 8.22 (s, 1H); MS (CI) m/z 456.2 [M+1].

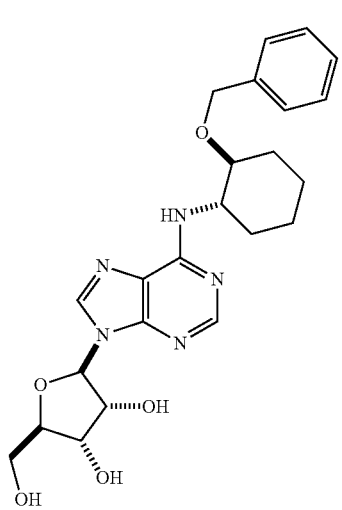

Compound 5: (2R,3R,4S,5R)-2-(6-((1S,2S)-2-(benzyloxy)cyclohexylamino)-9H-purin-9-yl)-5-(hydroxymethyptetrahydrofuran-3,4-diol ¹H NMR (CDCl₃) δ 1.27-1.48 (m, 4H), 1.69-1.83 (m, 2H), 2.11-2.29 (m, 2H), 3.04 (s, 1H), 3.28-3.35 (m, 1H), 3.74 (d, J=10.8 Hz, 1H), 3.94 (d, J=12.9 Hz, 1H), 4.33 (s, 2H), 4.42 (d, J=12 Hz, 1H), 4.43 (s, 1H), 4.63 (d, J=12 Hz, 1H), 5.06 (s, 1H), 5.74 (d, J=7.5 Hz, 1H), 5.78 (bs, 1H), 6.58 (d, J=11.1 Hz, 1H), 7.14-7.25 (m, 5H), 7.67 (s, 1H), 8.22 (s, 1H); MS (CI) m/z 456.2 [M+1].

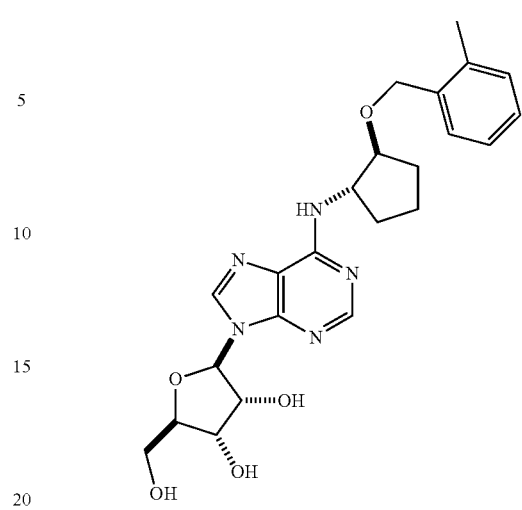

Compound 7: (2R,3S,4R,5R)-2-(hydroxymethyl)-5-(6-((1S,2S)-2-(2-methylbenzyloxy)cyclopentylamino)-9H-purin-9-yl)tetrahydrofuran-3,4-diol ¹H NMR (CDCl₃) δ 1.54-1.58 (m, 1H), 1.76-1.93 (m, 5H), 2.29 (s, 3H), 3.62-3.73 (m, 1H), 3.86-3.89 (m, 1H), 3.92 (s, 1H), 4.28 (s, 1H), 4.34 (d, J=4.8 Hz, 1H), 4.53-4.64 (m, 3H), 4.97-4.98 (m, 1H), 5.10 (s, 1H), 5.72 (d, J=7.2 Hz, 1H), 5.89 (s, 1H), 6.70 (s, 1H), 7.13-7.18 (m, 3H), 7.25-7.29 (m, 1H), 7.69 (s, 1H), 8.14 (s, 1H).

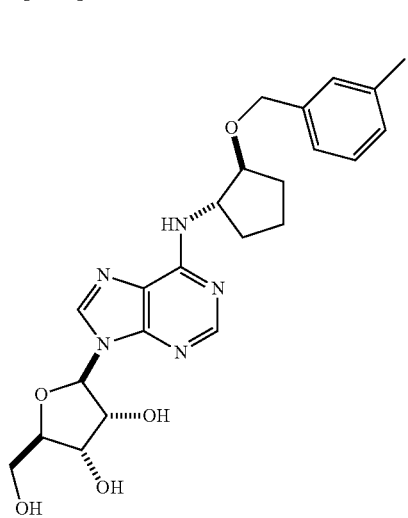

Compound 6: (2R,3S,4R,5R)-2-(hydroxymethyl)-5-(6-((1S,2S)-2-(3-methylbenzyloxy)cyclopentylamino)-9H-purin-9-yl)tetrahydrofuran-3,4-diol ¹H NMR (CDCl₃) δ 1.54-1.58 (m, 2H), 1.77-1.91 (m, 4H), 2.28 (s, 3H), 3.46 (s, 1H), 3.66-3.71 (m, 1H), 3.87 (s, 1H), 3.91 (s, 1H), 4.28 (s, 1H), 4.37 (d, J=4.8 Hz, 1H), 4.56-4.61 (m, 3H), 4.94-4.98 (m, 1H), 5.74 (d, J=6.9 Hz, 1H), 5.99 (s, 1H), 7.02-7.26 (m, 4H), 7.71 (s, 1H), 8.16 (s, 1H).

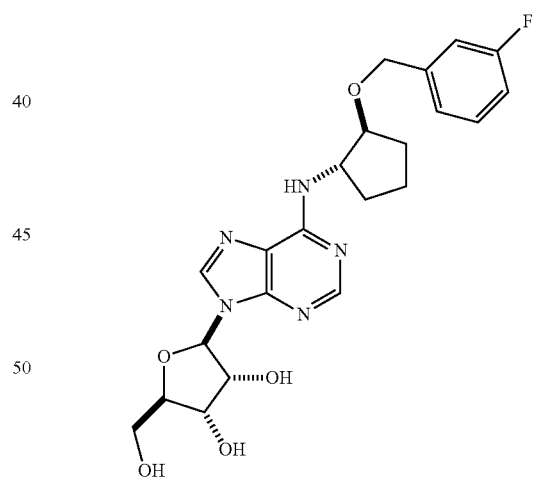

Compound 8: (2R,3R,4S,5R)-2-(6-((1S,2S)-2-(3-fluorobenzyloxy)cyclopentylamino)-9H-purin-9-yl)-5-(hydroxymethyl)tetrahydrofuran-3,4-diol ¹H NMR (CDCl₃) δ 1.55-1.62 (m, 1H), 1.77-1.93 (m, 5H), 2.28-2.34 (m, 1H), 3.56 (bs, 1H), 3.68-3.73 (m, 1H), 3.86-3.93 (m, 2H), 4.30 (s, 1H), 4.41 (d, J=4.2 Hz, 1H), 4.58-4.66 (m, 3H), 5.01-5.03 (m, 1H), 5.77 (d, J=6.9 Hz, 1H), 5.89 (s, 1H), 6.70 (s, 1H), 6.91-6.94 (m, 1H), 7.04 (d, J=8.7 Hz, 2H), 7.20-7.25 (m, 1H), 7.72 (s, 1H), 8.14 (s, 1H).

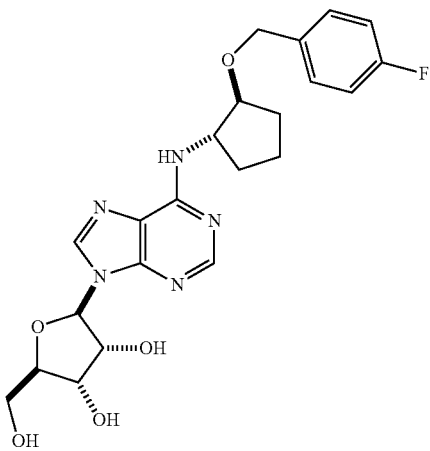

Compound 9: (2R,3R,4S,5R)-2-(6-(1S,2S)-2-(4-fluorobenzyloxy)cyclopentylamino)-9H-purin-9-yl)-5-(hydroxymethyl)tetrahydrofuran-3,4-diol ¹H NMR (CDCl₃) δ 1.56-1.60 (m, 2H), 1.75-1.91 (m, 5H), 2.26-2.30 (m, 1H), 3.57 (bs, 1H), 3.69-3.73 (m, 1H), 3.84-3.94 (m, 2H), 4.30 (s, 1H), 4.41 (d, J=4.2 Hz, 1H), 4.57-4.62 (m, 3H), 5.01-5.03 (m, 2H), 5.76 (d, J=6.9 Hz, 1H), 5.90 (d, J=6.3 Hz, 1H), 6.71 (s, 1H), 6.93-6.99 (m, 2H), 7.24-7.28 (m, 2H), 7.72 (s, 1H), 8.14 (s, 1H).

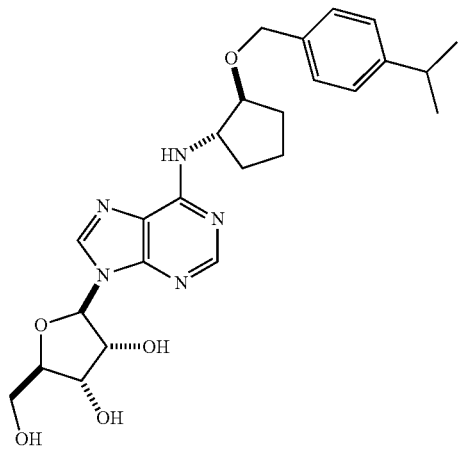

Compound 10: (2R,3S,4R,5R)-2-(hydroxymethyl)-5-(6-((1S,2S)-2-(4-isopropylbenzyloxy)cyclopentylamino)-9H-purin-9-yl)tetrahydrofuran-3,4-diol ¹H NMR (CDCl₃) δ 1.20 (d, J=6.9 Hz, 6H), 1.52-1.58 (m, 1H), 1.73-1.91 (m, 4H), 2.24-2.31 (m, 2H), 2.82-2.89 (m, 1H), 3.57 (bs, 1H), 3.67-3.71 (m, 1H), 3.84-3.92 (m, 3H), 4.27 (s, 1H), 4.36 (d, J=4.8 Hz, 1H), 4.52-4.61 (m, 3H), 4.94-4.98 (m, 1H), 5.74 (d, J=7.2 Hz, 1H), 5.96 (m, 1H), 6.76 (s, 1H), 7.14 (d, J=8.1 Hz, 2H), 7.22 (d, J=8.1 Hz, 2H), 7.70 (s, 1H), 8.14 (s, 1H).

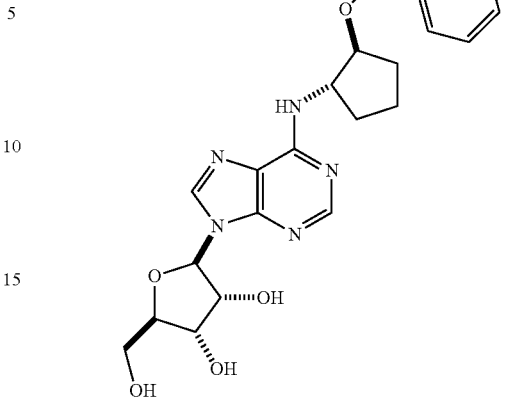

Compound 11: (2R,3S,4R,5R)-2-(hydroxymethyl)-5-(6-((1S,2S)-2-(3-iodobenzyloxy)cyclopentylamino)-9H-purin-9-yl)tetrahydrofuran-3,4-diol ¹H NMR (CDCl₃) δ 1.55-1.64 (m, 1H), 1.74-1.96 (m, 5H), 2.25-2.34 (m, 1H), 3.40 (s, 1H), 3.67-3.74 (m, 1H), 3.84-3.93 (m, 2H), 4.31 (s, 1H), 4.42 (d, J=4.8 Hz, 1H), 4.56-4.61 (m, 3H), 5.01-5.05 (dd, J=6.6 and 5.4 Hz, 1H), 5.76 (d, J=7.2 Hz, 1H), 5.85 (bs, 1H), 6.67 (d, J=9.6 Hz, 1H), 6.98-7.03 (dd, J=7.5 and 7.8 Hz, 1H), 7.21-2.25 (m, 2H), 7.54 (d, J=7.5 Hz, 1H), 7.65 (s, 1H), 7.73 (s, 1H), 8.16 (s, 1H)

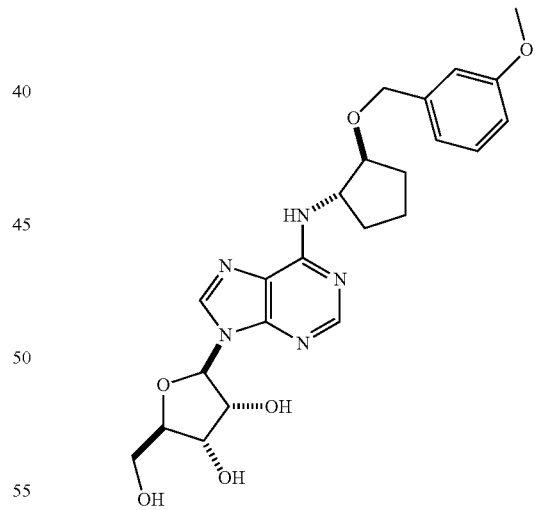

Compound 12: (2R,3S,4R,5R)-2-(hydroxymethyl)-5-(6-((1S,2S)-2-(3-methoxybenzyloxy)cyclopenty-lamino)-9H-purin-9-yl)tetrahydrofuran-3,4-diol ¹H NMR (CDCl₃) δ 1.53-1.60 (m, 1H), 1.75-1.93 (m, 5H), 2.27-2.34 (m, 1H), 2.67-3.73 (m, 1H), 3.74 (s, 3H), 3.84-3.92 (m, 2H), 4.29 (s, 1H), 4.39 (d, J=4.5 Hz, 1H), 4.59 (s, 1H), 4.97-5.01 (dd, J=6.6 and 5.4 Hz, 1H), 5.75 (d, J=7.2 Hz, 1H), 5.90 (bs, 1H), 6.64-6.78 (m, 2H), 6.86-6.87 (m, 2H), 7.19 (dd, J=7.8 and 8.1 Hz, 1H), 7.25 (s, 1H), 7.70 (s, 1H), 8.15 (s, 1H)

(d, J=6.9 Hz, 1H), 5.99-6.03 (m, 2H), 7.12-7.16 (m, 4H), 7.31-7.33 (m, 1H), 7.75 (s, 1H).

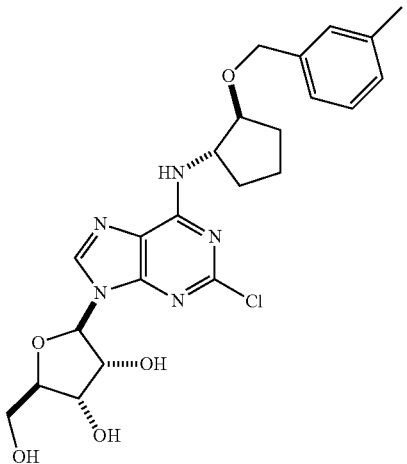

Compound 13: (2R,3R,4S,5R)-2-(2-chloro-6-((1S, 2S)-2-(3-methylbenzyloxy)cyclopentylamino)-9H-purin-9-yl)-5-(hydroxymethyptetrahydrofuran-3,4-diol $^1$H NMR (CDCl$_3$) δ 1.54-1.58 (m, 2H), 1.77-1.91 (m, 4H), 2.22-2.34 (m, 1H), 2.30 (s, 3H), 3.27 (s, 1H), 3.48 (s, 1H), 3.70-3.95 (m, 4H), 4.30 (s, 1H), 4.37 (d, J=4.8 Hz, 1H), 4.54-4.77 (m, 3H), 5.03 (s, 1H), 5.74 (d, J=6.9 Hz, 1H), 6.02 (s, 1H), 6.12 (d, J=10.8 Hz, 1H), 7.04 (d, J=7.2 Hz, 1H), 7.14-7.22 (m, 3H), 7.75 (s, 1H).

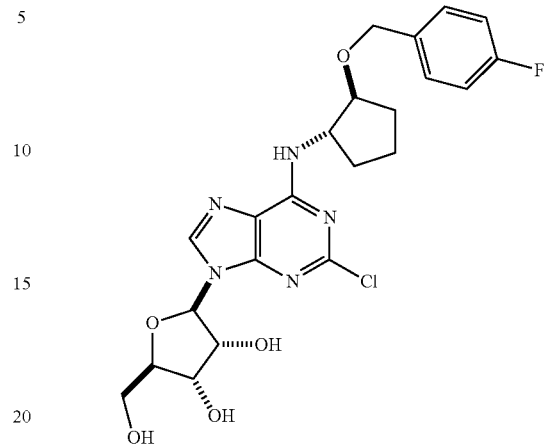

Compound 15: (2R,3R,4S,5R)-2-(2-chloro-6-((1S, 2S)-2-(4-fluorobenzyloxy)cyclopentylamino)-9H-purin-9-yl)-5-(hydroxymethyptetrahydrofuran-3,4-diol $^1$H NMR (CDCl$_3$) δ 1.54-1.56 (m, 1H), 1.72-1.91 (m, 4H), 1.85-1.90 (m, 1H), 2.25-2.30 (m, 1H), 3.26 (s, 1H), 3.70-3.82 (m, 3H), 3.94 (d, J=12.9 Hz, 1H), 4.31 (s, 1H), 4.38 (d, J=4.8 Hz, 1H), 4.52-4.76 (m, 3H), 5.02-5.04 (m, 1H), 5.75 (d, J=6.9 Hz, 1H), 5.99-6.01 (m, 2H), 6.10 (d, J=11.4 Hz, 1H), 6.99 (t, J=8.7 Hz, 2H), 7.30-7.33 (m, 2H), 7.77 (s, 1H).

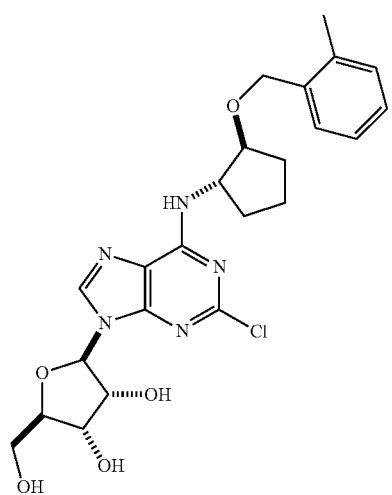

Compound 14: (2R,3R,4S,5R)-2-(2-chloro-6-((1S, 2S)-2-(2-methylbenzyloxy)cyclopentylamino)-9H-purin-9-yl)-5-(hydroxymethyptetrahydrofuran-3,4-diol $^1$H NMR (CDCl$_3$) δ 1.54-1.91 (m, 6H), 2.22-2.34 (m, 1H), 2.31 (s, 3H), 3.11 (s, 1H), 3.74 (dd, J=11.4 and 12.6 Hz, 1H), 3.87-3.96 (m, 2H), 4.31 (s, 1H), 4.39 (d, J=4.8 Hz, 1H), 4.54-4.58 (m, 3H), 4.74 (d, J=12 Hz, 1H), 5.03 (m, 1H), 5.74

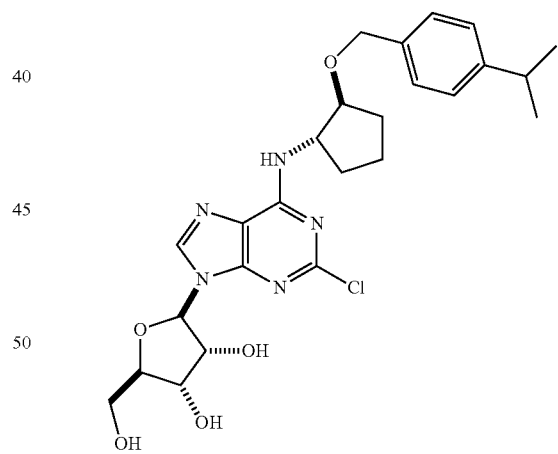

Compound 16: (2R,3R,4S,5R)-2-(2-chloro-6-((1S, 2S)-2-(4-isopropylbenzyloxy)cyclopentylamino)-9H-purin-9-yl)-5-(hydroxymethyptetrahydrofuran-3,4-diol $^1$H NMR (CDCl$_3$) δ 1.21 (d, J=6.9 Hz, 6H), 1.54-1.58 (m, 1H), 1.70-1.91 (m, 5H), 2.26-2.32 (m, 1H), 2.82-2.90 (m, 1H), 3.48 (s, 1H), 3.74 (t, J=11.7 Hz, 1H), 3.84 (s, 1H), 3.94 (d, J=12.9 Hz, 1H), 4.30 (s, 1H), 4.38 (d, J=4.8 Hz, 1H), 4.52-4.76 (m, 3H), 5.01-5.05 (m, 1H), 5.75 (d, J=6.9 Hz, 1H), 6.01 (d, J=6 Hz, 1H), 6.11 (d, J=11.4 Hz, 1H), 7.16 (d, J=7.8 Hz, 2H), 7.25-7.28 (m, 2H), 7.75 (s, 1H).

4.94 (s, 1H), 5.73 (d, J=7.2 Hz, 1H), 6.05 (bs, 1H), 7.13 (s, 2H), 7.29-7.30 (m, 1H), 7.74 (s, 1H), 8.17 (s, 1H).

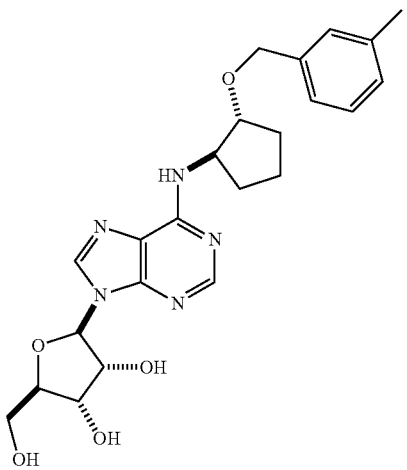

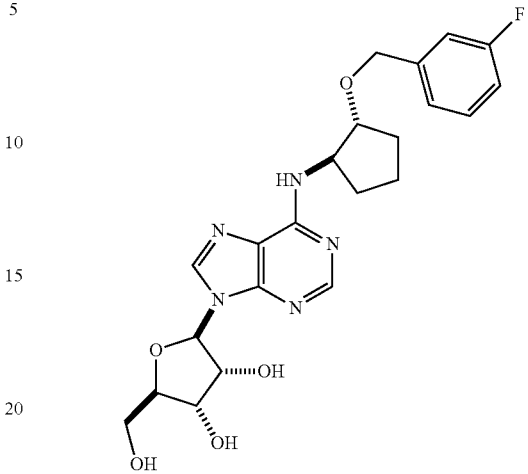

Compound 17: (2R,3S,4R,5R)-2-(hydroxymethyl)-5-(6-((1R,2R)-2-(3-methylbenzyloxy)cyclopentylamino)-9H-purin-9-yl)tetrahydrofuran-3,4-diol Compound 19: (2R,3R,4S,5R)-2-(6-((1R,2R)-2-(3-fluorobenzyloxy)cyclopentylamino)-9H-purin-9-yl)-5-(hydroxymethyl)tetrahydrofuran-3,4-diol ¹H NMR (CDCl₃) δ 1.54-1.58 (m, 2H), 1.77-1.98 (m, 4H), 2.29 (s, 3H), 3.47 (s, 1H), 3.68 (d, J=12 Hz, 1H), 3.90 (d, J=11.7 Hz, 2H), 4.29 (s, 1H), 4.40 (d, J=4.8 Hz, 1H), 4.58 (s, 2H), 4.94-4.98 (m, 1H), 5.74 (d, J=6.9 Hz, 1H), 6.01 (bs, 1H), 7.03-7.20 (m, 4H), 7.73 (s, 1H), 8.15 (s, 1H).

¹H NMR (CDCl₃) δ 1.52-1.58 (m, 1H), 1.73-1.98 (m, 4H), 2.25-2.32 (m, 1H), 3.70 (d, J=11.7 Hz, H), 3.90 (d, J=11.1 Hz, 2H), 4.28 (s, 1H), 4.40 (d, J=4.2 Hz, 1H), 4.61 (bs, 3H), 4.98-4.96 (m, 1H), 5.77 (d, J=6.9 Hz, 1H), 6.89 (t, J=9 Hz, 1H), 7.08 (d, J=7.8 Hz, 2H), 7.22 (m, 1H), 7.79 (s, 1H), 8.17 (s, 1H).

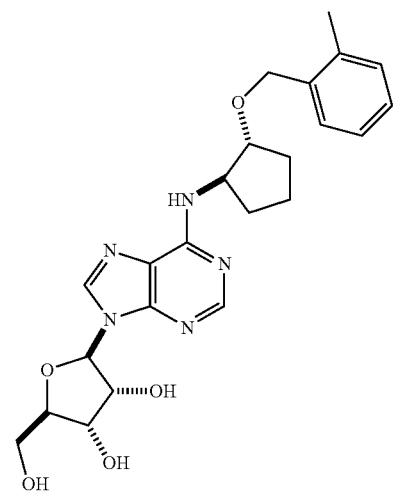

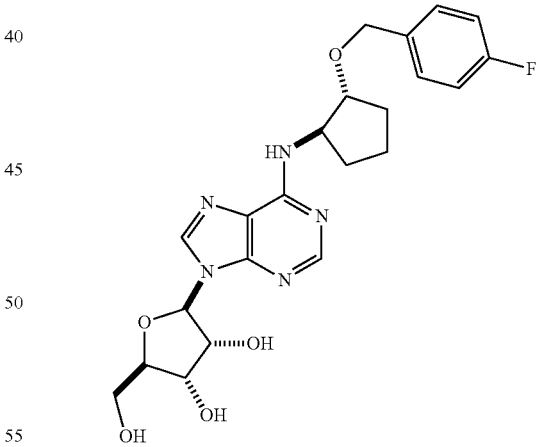

Compound 18: (2R,3S,4R,5R)-2-(hydroxymethyl)-5-(6-((1R,2R)-2-(2-methylbenzyloxy)cyclopentylamino)-9H-purin-9-yl)tetrahydrofuran-3,4-diol Compound 20: (2R,3R,4S,5R)-2-(6-((1R,2R)-2-(4-fluorobenzyloxy)cyclopentylamino)-9H-purin-9-yl)-5-(hydroxymethyl)tetrahydrofuran-3,4-diol ¹H NMR (CDCl₃) δ 1.52-1.56 (m, 1H), 1.74-1.97 (m, 5H), 2.31 (s, 3H), 3.70 (d, J=12.6 Hz, 1H), 3.86-3.89 (m, 1H), 3.92 (s, 1H), 4.28 (s, 1H), 4.34 (d, J=4.8 Hz, 1H), 4.53-3.90 (d, J=12.3 Hz, 2H), 4.29 (s, 1H), 4.40 (s, 1H), 4.56-4.66 (m, 3H), ¹H NMR (CDCl₃) δ 1.52-1.56 (m, 1H), 1.75-1.96 (m, 4H), 2.25-2.30 (m, 1H), 3.68-3.72 (m, 1H), 3.86-3.93 (m, 2H), 4.29 (s, 1H), 4.40 (d, J=4.2 Hz, 1H), 4.58 (m, 3H), 4.94-4.98

(m, 1H), 5.76 (d, J=6.9 Hz, 1H), 6.04 (s, 1H), 6.96 (t, J=8.4 Hz, 2H), 7.25-7.28 (m, 2H), 7.78 (s, 1H), 8.15 (s, 1H).

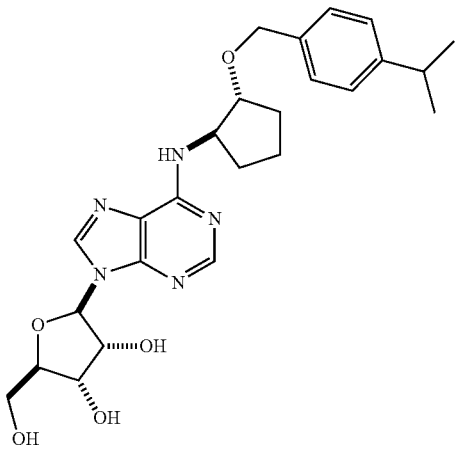

Compound 21: (2R,3S,4R,5R)-2-(hydroxymethyl)-5-(6-(((1R,2R)-2-(4-isopropylbenzyloxy)cyclopentylamino)-9H-purin-9-yl)tetrahydrofuran-3,4-diol: ¹H NMR (CDCl₃) δ 1.22 (d, J=6.9 Hz, 6H), 1.52-1.97 (m, 5H), 2.27-2.32 (m, 2H), 2.82-2.90 (m, 1H), 3.19 (bs, 1H), 3.71 (d, J=13.2 Hz, 1H), 3.92 (d, J=11.7 Hz, 2H), 4.30 (s, 1H), 4.60 (m, 2H), 4.97-5.01 (m, 1H), 5.74 (d, J=7.2 Hz, 1H), 5.94 (d, J=7.5 Hz, 1H), 6.54 (s, 1H), 7.16 (d, J=8.1 Hz, 2H), 7.26 (d, J=8.1 Hz, 2H), 7.73 (s, 1H), 8.19 (s, 1H)

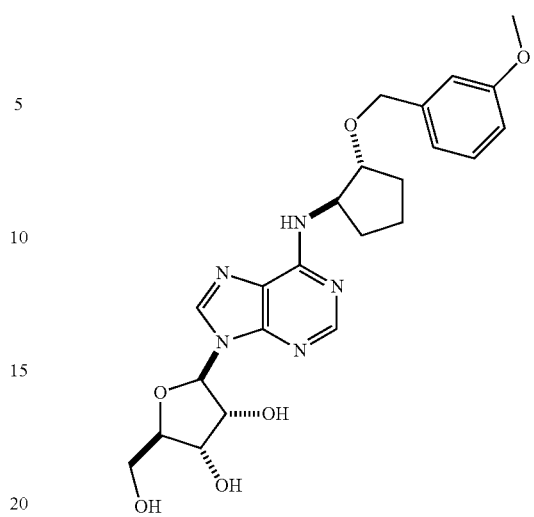

Compound 23: (2R,3S,4R,5R)-2-(hydroxymethyl)-5-(6-(((1R,2R)-2-(3-methoxybenzyloxy)cyclopentylamino)-9H-purin-9-yl)tetrahydrofuran-3,4-diol ¹H NMR (CDCl₃) δ 1.51-1.65 (m, 1H), 1.74-1.96 (m, 5H), 2.26-2.31 (m, 1H), 2.67-3.73 (m, 1H), 3.70-3.73 (m 1H), 3.74 (s, 3H), 3.88-3.92 (m, 2H), 4.29 (s, 1H), 4.39 (d, J=4.5 Hz, 1H), 4.60 (s, 2H), 4.95-4.99 (dd, J=6.6 and 5.4 Hz, 1H), 5.74 (d, J=7.2 Hz, 1H), 5.97 (d, J=7.8 Hz, 1H), 6.62 (bs, 1H), 6.75 (d, J=7.8 Hz, 2H), 6.88-6.91 (m, 1H), 7.19 (dd, J=7.8 and 8.1 Hz, 1H), 7.25 (s, 1H), 7.73 (s, 1H), 8.17 (s, 1H).

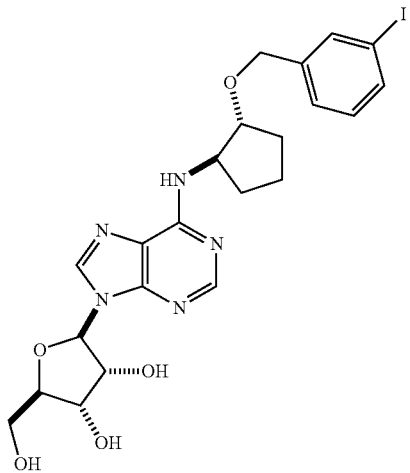

Compound 22: (2R,3S,4R,5R)-2-(hydroxymethyl)-5-(6-(((1R,2R)-2-(3-iodobenzyloxy)cyclopentylamino)-9H-purin-9-yl)tetrahydrofuran-3,4-diol ¹H NMR (CDCl₃) δ 1.54-1.64 (m, 1H), 1.71-1.96 (m, 5H), 2.26-2.32 (m, 1H), 3.68-3.74 (m, 1H), 3.90-3.95 (m, 2H), 4.32 (s, 1H), 4.42 (d, J=4.8 Hz, 1H), 4.57-4.61 (m, 3H), 4.98-5.03 (dd, J=5.7 and 6.0 Hz, 1H), 5.76 (d, J=7.2 Hz, 1H), 5.89 (d, J=7.8 Hz, 1H), 6.60 (bs, 1H), 6.98-7.04 (dd, J=7.8 and 8.1 Hz, 1H), 7.25-2.29 (m, 2H), 7.54 (d, J=7.5 Hz, 1H), 7.68 (s, 1H), 7.76 (s, 1H), 8.22 (s, 1H)

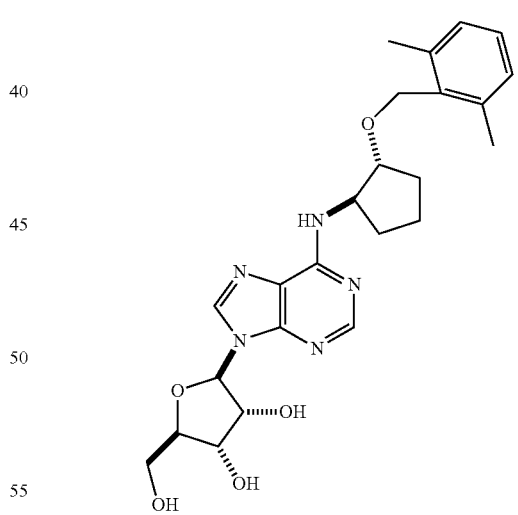

Compound 24: (2R,3S,4R,5R)-2-(hydroxymethyl)-5-(6-(((1R,2R)-2-(2,6-dimethylbenzyloxy)cyclopentylamino)-9H-purin-9-yl)tetrahydrofuran-3,4-diol ¹H NMR (CDCl₃) δ 1.6-1.9 (m, 5H), 1.95-2.1 (m, 1H), 2.27-2.31 (m, 1H), 2.38 (s, 6H), 3.20 (s, 1H), 3.71 (m, 1H), 3.90 (2, J=13.2 Hz, 1H), 4.30 (s, 1H), 4.41 (s, 1H), 4.53 (d, J=9 Hz, 1H), 4.70 (d, J=10.2 Hz, 1H), 4.96 (s, 1H), 5.70 (d, J=7.2 Hz, 1H), 5.94 (bs, 1H), 6.57 (s, 1H), 6.97-7.06 (m, 3H), 7.25 (s, 1H), 7.72 (s, 1H), 8.19 (s, 1H).

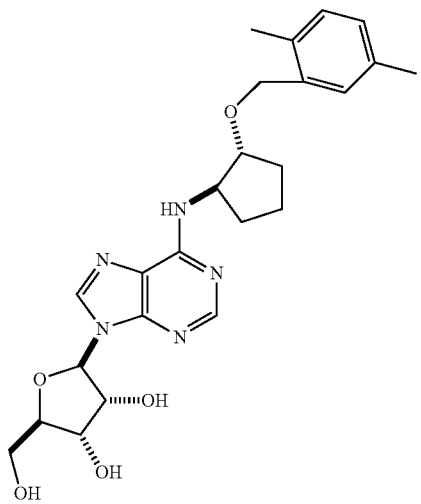

Compound 25: (2R,3S,4R,5R)-2-(hydroxymethyl)-5-(6-(((1R,2R)-2-(2,5-dimethylbenzyloxy)cyclopentylamino)-9H-purin-9-yl)tetrahydrofuran-3,4-diol $^1$H NMR (CDCl$_3$) δ 1.51-1.58 (m, 1H), 1.74-1.96 (m, 4H), 1.96-2.10 (m, 1H), 2.25 (s, 6H), 3.43 (s, 2H), 3.70 (s, 1H), 3.90 (d, J=12.9 Hz, 2H), 4.28 (s, 1H), 4.39 (d, J=4.5 Hz, 1H), 4.56-4.63 (m, 2H), 4.75 (s, 1H), 4.95 (s, 1H), 5.71 (d, J=7.2 Hz, 1H), 6.02 (d, J=6.9 Hz, 1H), 6.63 (s, 1H), 6.94 (d, J=7.8 Hz, 1H), 7.01 (d, 7.8 Hz, 1H), 7.13 (s, 1H), 7.25 (s, 1H), 7.71 (s, 1H), 8.18 (s, 1H).

Adenosine Receptor Binding Studies:

The compounds were studied in binding assays to determine their selectivity and potency to the $A_1$, $A_{2a}$ and $A_3$ adenosine receptors. The results are shown below in the following table.

| Compound | $(A_1)^a$ Ki (nM) | $(A_{2a})^b$ Ki (nM) | $(A_3)^c$ Ki (nM) |
| --- | --- | --- | --- |
| 1 | 1.72 | 476 | 2,620 |
| 2 | 2.97 | 2,530 | 820 |
| 3 | 29 | 25,400 | 2,550 |
| 4 | 53.1 | 3,740 | >100,000 |
| 5 | 1360 | >100,000 | >100,000 |
| 6 | 2.79 | 5,320 | 1,350 |
| 7 | 12.6 | 7,330 | 1,570 |
| 8 | 3.61 | 5,540 | 1,630 |
| 9 | 14.4 | 11,400 | 1,870 |
| 10 | 28.8 | 6,830 | 1,290 |
| 11 | 3.68 | 2,980 | 1,290 |
| 12 | 12.3 | 9,370 | 2,300 |
| 13 | nt | nt | nt |
| 14 | nt | nt | nt |
| 15 | nt | nt | nt |
| 16 | nt | nt | nt |
| 17 | 2.65 | 3,370 | 2,620 |
| 18 | 2.28 | 422 | 5,100 |
| 19 | 3.53 | 2,550 | 4,040 |
| 20 | 6.08 | 3,780 | 3,710 |
| 21 | 6.06 | 15,600 | 3,380 |
| 22 | 5.59 | 2,770 | 551 |
| 23 | 4.86 | 2,270 | 3,370 |

[a]Displacement of specific [$^3$H]CCPA binding in CHO cells stably transfected with human recombinant A$_1$ adenosine receptor, expressed as Ki (nM).
[b]Displacement of specific [$^3$H]NECA binding in CHO cells stably transfected with human recombinant A$_{2A}$ adenosine receptor, expressed as Ki (nM).
[c]Displacement of specific [$^3$H]NECA binding in CHO cells stably transfected with human recombinant A$_3$ adenosine receptor, expressed as Ki (nM).

It can be seen from the above table that the compounds are potent A1 agonists, while also being very selective to the A1 receptor over the A2a and A3 receptors. The c Log P values for the compounds are predominantly between 2 and 3.5 and with such c Log P values it is anticipated that these compounds will cross the human corneal barrier.

Evaluation of Compounds 1, 11, 17 and 18 in Rabbits for Changes in Intraocular Pressure A study was conducted using ocular normotensive Dutch-Belted rabbits to evaluate changes in the intraocular pressure (TOP) of compounds 1, 11, 17 and 18 following topical administration to an eye of a rabbit.

The study involved groups of eight rabbits and the rabbits were acclimated for two days before they received a single dose in either the right eye or left eye of the HPCD control. The IOP of the groups of rabbits were recorded at 0, 1, 2, 4 and 6 hours after dosing of the control. The following day Compound 1 was administered as a single dose (200 mcg), as a formulation comprising 1 part of an $A_1$ agonist to 15 parts Hydroxypropyl β-Cyclodextrin (HPβCD) in WFI (i.e. 1:15 wt/wt) reconstituted with 0.9% Saline for Injection, to the right eye of one group of eight rabbits and IOP measurements were recorded at 0, 1, 2, 4 and 6 hours after dosing of Compound 1. The rabbits eyes were then washed out and three days later three groups of 8 rabbits were then administered a single dose (200 mcg) to the left eye and IOP measurements were recorded at 0, 1, 2, 4 and 6 hours after dosing with one of Compounds 11, 17 or 18.

Figure 2A:
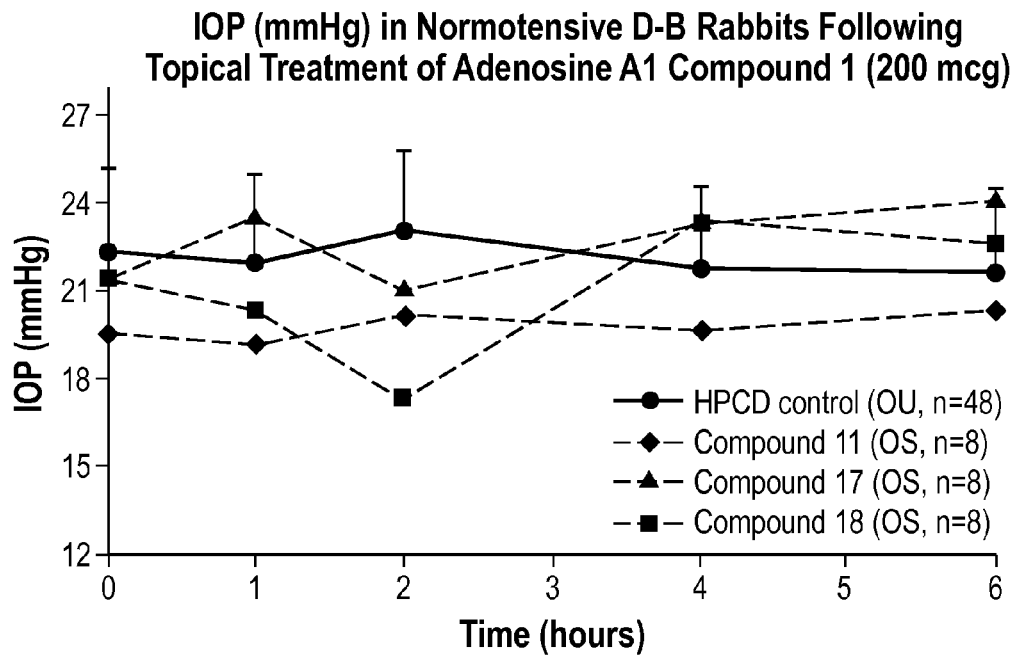
FIG. 2a: shows the IOP (mmHg) changes over time in the study eye of three groups of Normotensive Dutch-Belted rabbits after administration of a topical single dose of 200 mcg of Compound 11, Compound 17 or Compound 18, relative to a HPCD control group.
Figure 2B:
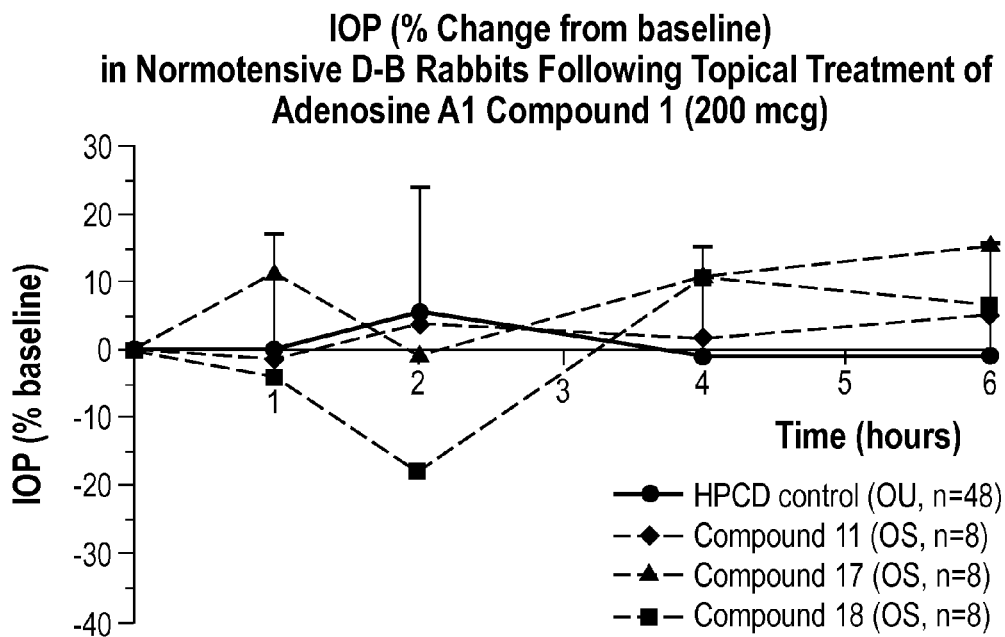
FIG. 2b: shows the IOP (% change from baseline) changes over time in the study eye of three groups of Normotensive Dutch-Belted rabbits after administration of a topical single dose of 200 mcg of Compound 11, Compound 17 or Compound 18, relative to a HPCD control group.

The results are shown in FIGS. 1a, 1b, 2a and 2b. It can be seen from FIGS. 1a and 1b that Compound 1 shows 28% reduction of IOP in normotensive Dutch-Belted rabbits at 2 hours post dosing, with a return of IOP to baseline levels 6 hours post dosing. FIGS. 2a and 2b show that Compounds 11 and 17 do not show significant changes in IOP relative to baseline after dosing. However, Compound 18 does show a reduction in IOP with the maximum (i.e 20%) IOP reduction measured at 2 hours post dosing, with a return of IOP to baseline levels 6 hours post dosing.

Furthermore, given the selectivity and potency towards the A1 receptor of these compounds they may be useful for treating a condition whereby agonism of the A1 receptor is desirable, such as reducing the intraocular pressure in a subject's eye, slowing a subject's metabolic rate, treating pain, protecting a subject's heart against myocardial damage during cardioplegia, treating a cardiovascular disease including cardiac arrhythmia, congestive heart failure, or cardiomyopathy.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

The invention claimed is:
1. A compound of Formula (I)

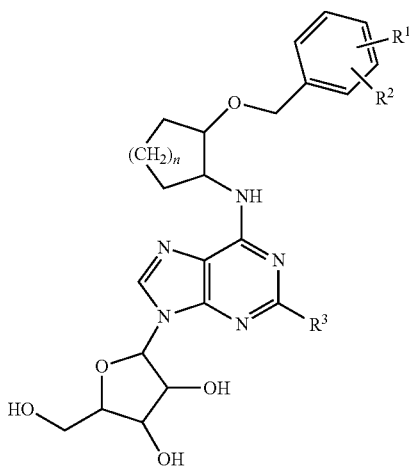

or a pharmaceutically acceptable salt thereof,
wherein, $R^1$ and $R^2$ are independently selected from the group consisting of —H, —$C_1$-$C_6$alkyl, -halo, and —O($C_1$-$C_6$)alkyl;
$R^3$ is selected from the group consisting of —H, -halo and —CN; and n is 1 or 2, with the proviso that the compound

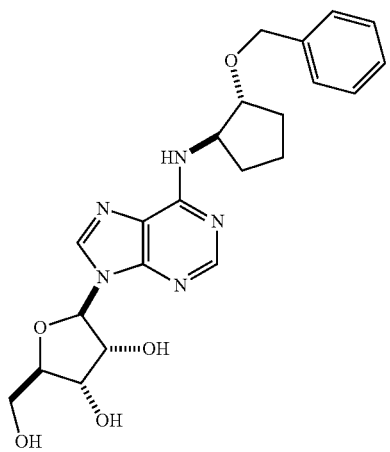

and its stereoisomers are excluded.

2. The compound of claim 1 wherein n is 1, $R^1$ is —$C_1$-$C_6$alkyl, $R^2$ is —H and $R^3$ is —H.
3. The compound of claim 1 wherein n is 1, $R^1$ is —H, $R^2$ is —H and $R^3$ is -halo.
4. The compound of claim 1 wherein n is 1, $R^1$ is —H, $R^2$ is —H and $R^3$ is —Cl.
5. The compound of claim 1 wherein n is 1, $R^1$ is —CH($CH_3$)$_2$, $R^2$ is —H and $R^3$ is —H.
6. The compound of claim 1 wherein n is 1, $R^1$ is —$CH_3$, $R^2$ is —H and $R^3$ is —H.
7. The compound of claim 1 wherein n is 1, $R^1$ is —$CH_3$, $R^2$ is —H and $R^3$ is -halo.
8. The compound of claim 1 wherein n is 1, $R^1$ is —$CH_3$, $R^2$ is —H and $R^3$ is —Cl.
9. The compound of claim 1 wherein n is 1, $R^1$ is halo, $R^2$ is —H and $R^3$ is -halo.
10. The compound of claim 1 wherein n is 1, $R^1$ is —F, $R^2$ is —H and $R^3$ is —Cl.
11. The compound of claim 1 wherein n is 1, $R^1$ is —CH($CH_3$)$_2$, $R^2$ is —H and $R^3$ is -halo.
12. The compound of claim 1 wherein n is 1, $R^1$ is halo, $R^2$ is —H and $R^3$ is H.
13. The compound of claim 1 wherein n is 1, $R^1$ is —F, $R^2$ is —H and $R^3$ is H.
14. The compound of claim 1 wherein n is 1, $R^1$ is —I, $R^2$ is —H and $R^3$ is H.
15. The compound of claim 1 wherein n is 1, $R^1$ is —O($C_1$-$C_6$)alkyl, $R^2$ is —H and $R^3$ is H.
16. The compound of claim 1 wherein n is 1, $R^1$ is —$OCH_3$, $R^2$ is —H and $R^3$ is H.
17. The compound of claim 1 wherein n is 1, $R^1$ is —$CH_3$, $R^2$ is —$CH_3$ and $R^3$ is H.
18. The compound of claim 1 wherein n is 2, $R^1$ is —H, $R^2$ is —H and $R^3$ is H.
19. The compound of claim 1 wherein n is 2, $R^1$ is —H, $R^2$ is —H and $R^3$ is -halo.
20. The compound of claim 1 wherein n is 2, $R^1$ is —H, $R^2$ is —H and $R^3$ is —Cl.
21. The compound of claim 1 wherein n is 2, $R^1$ is —CH($CH_3$)$_2$, $R^2$ is —H and $R^3$ is H.
22. The compound of claim 1 wherein n is 2, $R^1$ is —$CH_3$, $R^2$ is —H and $R^3$ is H.
23. The compound of claim 1 wherein n is 2, $R^1$ is —$CH_3$, $R^2$ is —H and $R^3$ is -halo.
24. The compound of claim 1 wherein n is 2, $R^1$ is —$CH_3$, $R^2$ is —H and $R^3$ is —Cl.
25. The compound of claim 1 wherein n is 2, $R^1$ is halo, $R^2$ is —H and $R^3$ is -halo.
26. The compound of claim 1 wherein n is 2, $R^1$ is —F, $R^2$ is —H and $R^3$ is —Cl.
27. The compound of claim 1 wherein n is 2, $R^1$ is —CH($CH_3$)$_2$, $R^2$ is —H and $R^3$ is -halo.
28. The compound of claim 1 wherein n is 2, $R^1$ is halo, $R^2$ is —H and $R^3$ is H.
29. The compound of claim 1 wherein n is 2, $R^1$ is —F, $R^2$ is —H and $R^3$ is H.
30. The compound of claim 1 wherein n is 2, $R^1$ is —I, $R^2$ is —H and $R^3$ is H.
31. The compound of claim 1 wherein n is 2, $R^1$ is —O($C_1$-$C_6$)alkyl, $R^2$ is —H and $R^3$ is H.
32. The compound of claim 1 wherein n is 2, $R^1$ is —$OCH_3$, $R^2$ is —H and $R^3$ is H.
33. The compound of claim 1 wherein n is 2, $R^1$ is —$CH_3$, $R^2$ is —$CH_3$ and $R^3$ is H.
34. The compound of claim 1 wherein the compound of Formula (I) or a pharmaceutically acceptable salt thereof, is selected from the group consisting of:
   2-(6-(2-(benzyloxy)cyclohexylamino)-9H-purin-9-yl)-5-(hydroxymethyl)tetrahydrofuran-3,4-diol;
   2-(hydroxymethyl)-5-(6-(2-(4-methylbenzyloxy)cyclopentylamino)-9H-purin-9-yl)tetrahydrofuran-3,4-diol;
   2-(hydroxymethyl)-5-(6-(2-(3-methylbenzyloxy)cyclopentylamino)-9H-purin-9-yl)tetrahydrofuran-3,4-diol;
   2-(hydroxymethyl)-5-(6-(2-(2-methylbenzyloxy)cyclopentylamino)-9H-purin-9-yl)tetrahydrofuran-3,4-diol;
   2-(6-(2-(3-fluorobenzyloxy)cyclopentylamino)-9H-purin-9-yl)-5-(hydroxymethyl)tetrahydrofuran-3,4-diol;
   2-(6-(2-(4-fluorobenzyloxy)cyclopentylamino)-9H-purin-9-yl)-5-(hydroxymethyl)tetrahydrofuran-3,4-diol;

2-(hydroxymethyl)-5-(6-(2-(4-isopropylbenzyloxy)cyclopentylamino)-9H-purin-9-yl)tetrahydrofuran-3,4-diol;
2-(hydroxymethyl)-5-(6-(2-(3-iodobenzyloxy)cyclopentylamino)-9H-purin-9-yl)tetrahydrofuran-3,4-diol;
2-(hydroxymethyl)-5-(6-(2-(3-methoxybenzyloxy)cyclopentylamino)-9H-purin-9-yl)tetrahydrofuran-3,4-diol;
2-(2-chloro-6-(2-(3-methylbenzyloxy)cyclopentylamino)-9H-purin-9-yl)-5-(hydroxymethyl)tetrahydrofuran-3,4-diol;
2-(2-chloro-6-(2-(2-methylbenzyloxy)cyclopentylamino)-9H-purin-9-yl)-5-(hydroxymethyl)tetrahydrofuran-3,4-diol;
2-(2-chloro-6-(2-(4-fluorobenzyloxy)cyclopentylamino)-9H-purin-9-yl)-5-(hydroxymethyl)tetrahydrofuran-3,4-diol;
2-(2-chloro-6-(2-(4-isopropylbenzyloxy)cyclopentylamino)-9H-purin-9-yl)-5-(hydroxymethyl)tetrahydrofuran-3,4-diol;
2-(hydroxymethyl)-5-(6-(2-(2,6-dimethylbenzyloxy)cyclopentylamino)-9H-purin-9-yl)tetrahydrofuran-3,4-diol, and
2-(hydroxymethyl)-5-(6-(2-(2,5-dimethylbenzyloxy)cyclopentylamino)-9H-purin-9-yl)tetrahydrofuran-3,4-diol.

35. The compound of claim 1, wherein the compound of Formula I is

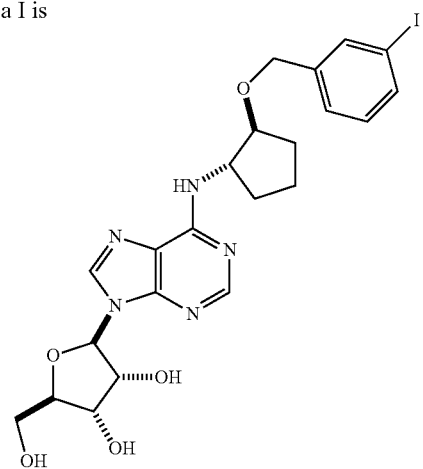

or pharmaceutically acceptable salt thereof.

36. The compound of claim 1, wherein the compound of Formula I is

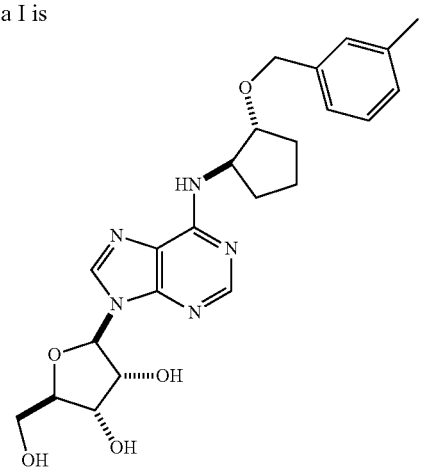

or pharmaceutically acceptable salt thereof.

37. The compound of claim 1, wherein the compound of Formula I is

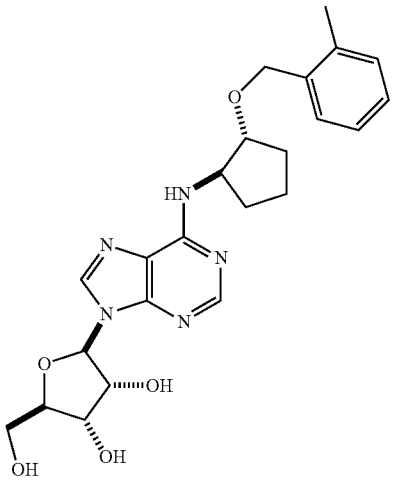

or pharmaceutically acceptable salt thereof.

38. A method of reducing intraocular pressure in a subject in need thereof, wherein said intraocular pressure is reduced through activation of the adenosine $A_1$ receptor, comprising administering to the anterior chamber of an affected eye of the subject, an effective amount of a compound of Formula I

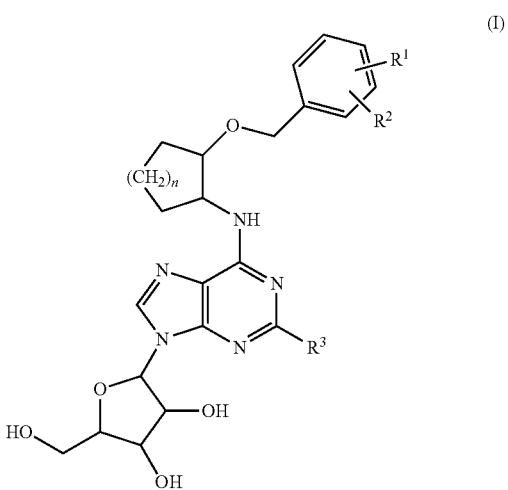

or a pharmaceutically acceptable salt thereof,
wherein, $R^1$ and $R^2$ are independently selected from the group consisting of —$C_1$-$C_6$alkyl, -halo, and —O($C_1$-$C_6$)alkyl; $R^3$ is selected from the group consisting of —H, -halo and —CN; and n is 1 or 2.

39. An ophthalmic pharmaceutical composition comprising a compound of Formula I as defined in claim 38 and a pharmaceutically acceptable vehicle or excipient, with the proviso that the compound
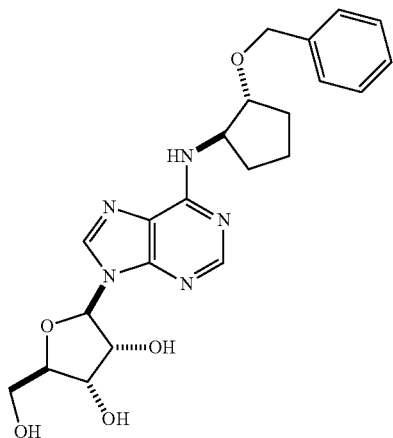
and its stereoisomers are excluded.
* * * * *

UNITED STATES PATENT AND TRADEMARK OFFICE
CERTIFICATE OF CORRECTION

| | |
|---|---|
| PATENT NO. | : 8,501,708 B2 |
| APPLICATION NO. | : 13/071993 |
| DATED | : August 6, 2013 |
| INVENTOR(S) | : Prakash Jagtap |

It is certified that error appears in the above-identified patent and that said Letters Patent is hereby corrected as shown below:

On the title page, column 1, insert the following new field:

--(63)   Related U.S. Application Data

U.S. 61/317,972 filed on March 26, 2010--

Signed and Sealed this
First Day of July, 2014

Michelle K. Lee
*Deputy Director of the United States Patent and Trademark Office*